(12) United States Patent
Foo et al.

(10) Patent No.: US 11,207,250 B2
(45) Date of Patent: Dec. 28, 2021

(54) ELASTOMERIC ARTICLES HAVING SKIN CARE PROPERTIES AND METHODS FOR THEIR PRODUCTION

(71) Applicant: SKINPROTECT CORPORATION SDN BHD, Selangor Darul Ehsan (MY)

(72) Inventors: Khon Pu Foo, Selangor Darul Ehsan (MY); Chin Keong Lim, Selangor Darul Ehsan (MY)

(73) Assignee: SKINPROTECT CORPORATION SDN BHD, Selangor (MY)

( * ) Notice: Subject to any disclaimer, the term of this patent is extended or adjusted under 35 U.S.C. 154(b) by 245 days.

(21) Appl. No.: 15/855,087

(22) Filed: Dec. 27, 2017

(65) Prior Publication Data

US 2018/0193237 A1    Jul. 12, 2018

(30) Foreign Application Priority Data

Dec. 30, 2016 (AU) ................................ 2016905394

(51) Int. Cl.
| | |
|---|---|
| *A61K 36/00* | (2006.01) |
| *A61K 8/14* | (2006.01) |
| *A61K 8/02* | (2006.01) |
| *A61Q 19/00* | (2006.01) |
| *A61K 8/9789* | (2017.01) |
| *A41D 19/015* | (2006.01) |
| *A61F 6/04* | (2006.01) |
| *A61B 42/10* | (2016.01) |
| *A41D 13/08* | (2006.01) |
| *A41D 19/00* | (2006.01) |
| *A61Q 19/08* | (2006.01) |
| *A61B 17/00* | (2006.01) |

(52) U.S. Cl.
CPC ............ *A61K 8/14* (2013.01); *A41D 13/087* (2013.01); *A41D 19/0082* (2013.01); *A41D 19/015* (2013.01); *A61B 42/10* (2016.02); *A61F 6/04* (2013.01); *A61K 8/0208* (2013.01); *A61K 8/0216* (2013.01); *A61K 8/9789* (2017.08); *A61Q 19/00* (2013.01); *A61Q 19/005* (2013.01); *A61Q 19/007* (2013.01); *A61Q 19/08* (2013.01); *A41D 2400/32* (2013.01); *A41D 2600/20* (2013.01); *A61B 2017/00526* (2013.01)

(58) Field of Classification Search
None
See application file for complete search history.

(56) References Cited

U.S. PATENT DOCUMENTS

| | | | |
|---|---|---|---|
| 6,274,154 B1 * | 8/2001 | Chou | ............ A61B 42/60 424/402 |
| 7,988,983 B2 | 8/2011 | Yu et al. | |
| 2004/0091504 A1 | 5/2004 | Hamann | |
| 2004/0122382 A1 | 6/2004 | Johnson et al. | |
| 2004/0126604 A1 * | 7/2004 | Wang | ............ A41D 19/0055 428/500 |
| 2005/0002995 A1 | 1/2005 | Schaller | |
| 2005/0132466 A1 | 6/2005 | Janssen et al. | |
| 2005/0222543 A1 | 10/2005 | Shao | |
| 2010/0316728 A1 | 12/2010 | Rreeves et al. | |
| 2014/0072619 A1 * | 3/2014 | Blum | ............ A61K 8/14 424/450 |
| 2015/0089714 A1 * | 4/2015 | Wang | ............ A41D 19/0055 2/161.7 |

FOREIGN PATENT DOCUMENTS

| | | | |
|---|---|---|---|
| CN | 104983666 A | 10/2015 | |
| DE | 201 00 269 U1 | 7/2001 | |
| EP | 2937075 A1 | 10/2015 | |
| WO | 97/38677 A2 | 10/1997 | |
| WO | 2004060338 A1 | 7/2004 | |
| WO | 2004060432 A1 | 7/2004 | |
| WO | 2008/011088 A2 | 1/2008 | |
| WO | 2008011088 A2 | 1/2008 | |
| WO | 2008053388 A1 | 5/2008 | |
| WO | 2009095821 A2 | 8/2009 | |
| WO | 2010104931 A1 | 9/2010 | |
| WO | 2013102882 A2 | 7/2013 | |
| WO | 2015/006807 A1 | 1/2015 | |
| WO | 2015/006808 A1 | 1/2015 | |
| WO | 2016069396 A2 | 5/2016 | |
| WO | WO-2016069396 A2 * | 5/2016 | ........... A61K 9/0014 |
| WO | 2017/127861 A1 | 8/2017 | |
| WO | 2017/127862 A1 | 8/2017 | |
| WO | 2017/127863 A1 | 8/2017 | |

OTHER PUBLICATIONS

Morus et al. (2014) Acta Poloniae Phramaceutica-Drug Research, vol. 71, No. 5, pp. 701-707. (Year: 2014).*
Trehan et al. (2017) Future Sci. OA 3(4): 5 pages (Year: 2017).*
Morus, M et al., "Plant stem cells as innovation in cosmetics", Acta Poloniae Pharmaceutica—Drug Research. vol. 71, No. 5, pp. 701-707, 2014 (in English).
Extended European Search Report, dated Mar. 7, 2020, issued in counterpart European Application No. 17888641.2 (in English; 7 pages).

* cited by examiner

*Primary Examiner* — Russell G Fiebig
(74) *Attorney, Agent, or Firm* — Westerman, Hattori, Daniels and Adrian, LLP

(57) ABSTRACT

The present application provides elastomeric articles that are able to deliver skin care properties to a person wearing or coming into contact with the article. The articles comprise an elastomeric film a plant stem cell material. The plant stem cell material may be in the form of a bilayer membrane-encapsulated plant stem cell material. The plant stem cell material may be present as a layer or coating on a surface of the elastomeric film. Also provided are methods for the production of the articles.

36 Claims, 6 Drawing Sheets

(A)

(B)

(A)

(B)

ELASTOMERIC ARTICLES HAVING SKIN CARE PROPERTIES AND METHODS FOR THEIR PRODUCTION

FIELD

The present invention relates to elastomeric articles having skin care properties, and methods for their production. The articles may be of a type intended for contact with the skin of a person. For example, the articles may be in the form of gloves that provide protection to the wearer while also providing skin care properties.

BACKGROUND

Gloves, such as thin film gloves, are worn in many industries for extended periods of time, and provide protection to the wearer from potentially dangerous materials and fluids that the wearer is required to contact in the course of their activities.

Typical gloves used in such situations are formed from elastomeric films with strong barrier properties. The gloves are made from thin films utilising relatively low cost elastomers, yielding a low unit price product, as they are intended to be changed frequently for reasons including hygiene and comfort.

While such gloves are readily available in a range of forms, there are very few variations available that are able to provide true skin care properties to the wearer of the gloves.

Some coated gloves are available. Such glove coatings usually provide a thin layer of a simple composition that provides an apparent skin moisturizing effect. However, such skin moisturising effects can in fact result from the false interpretation of the moisture felt by the skin following perspiration in the glove, combined with the coating material composition. Also described in the art are gloves containing coatings of simple plant extracts, such as *Aloe vera*, which are said to provide moisturising properties, particularly when combined with the sweat of the wearer's skin. However, such coatings again provide a superficial moisturising sensation. Furthermore, such plant extracts, after extraction from the plant and exposure to the environment, start to degrade on the surface of the glove during prolonged storage, so that the most effective components may no longer display significant bioactivity.

Another option for providing gloves with skin care properties involves coating the inner surface of the glove with a lotions or cream coating. However, a problem with such coatings is that these can deteriorate the glove performance, giving rise to adverse effects on the barrier and physical properties of the elastomer. Furthermore, such coatings can produce an uncomfortable greasy feeling. It is challenging to balance desirable properties such as tactile attributes with the therapeutic properties for the skin. Others in the art that have addressed such problems by using emollients such as glycerine and sorbitol (see WO2008/011088). However, the coatings have high viscosity and the conditions for applying the coatings (e.g. high temperature of application to make the composition more fluid, or the use of organic solvents) can give rise to difficulties in glove manufacturing operations.

The applicant has observed that glove coating technologies currently on the market do not take into account the properties required to effectively deliver a substance into the layer of the skin that is most important for effective skin protection and repair.

The applicant has considered the situation in the art and explored alternative ways to deliver skin care properties through the medium of elastomeric film articles such as gloves.

The applicant has also considered the impact that coatings on elastomeric films might have on the other desirable properties of the glove, including elasticity, modulus (fatigue associated with resistance of the glove), softness, film barrier properties, film thickness and cost. It would not be desirable to provide a new article having a coating that, while providing very effective skin care properties, impairs the barrier properties of the film, or adversely impacts on one or more other film properties.

It is an object of the applicant to provide new elastomeric articles, and methods for the production of such articles, that deliver skin care properties to the wearer of the articles, or at least to provide a useful alternative product.

SUMMARY

The applicant has developed new elastomeric articles that are able to deliver skin care properties to a person wearing or coming into contact with the article. These articles comprise an elastomeric film and contain a skin care component, which is based on plant stem cell material. The plant stem cell material may be applied through a suitable coating composition. The plant stem cell material may be bilayer membrane-encapsulated, or it may be combined with a phospholipid for the immobilisation of the skin care component on the film surface. The plant stem cell material, which may be in the form of bilayer membrane-encapsulated plant stem cell material or a blend of plant stem cell material and phospholipid, may be present as a layer or coating on a surface of the elastomeric film.

Thus, according to a first aspect, there is provided an elastomeric article comprising an elastomeric film and a plant stem cell material. In particular embodiments, the elastomeric article comprises an elastomeric film and a plant stem cell material on a surface thereof.

According to a second aspect, there is provided a method for the manufacture of an elastomeric article comprising an elastomeric film having skin care properties, the method comprising applying a plant stem cell material onto a surface of the elastomeric film.

BRIEF DESCRIPTION OF THE DRAWINGS

The present invention will now be described in further detail with reference to the following figures which illustrate non-limiting examples of aspects of the invention.

DETAILED DESCRIPTION

Figure 1:
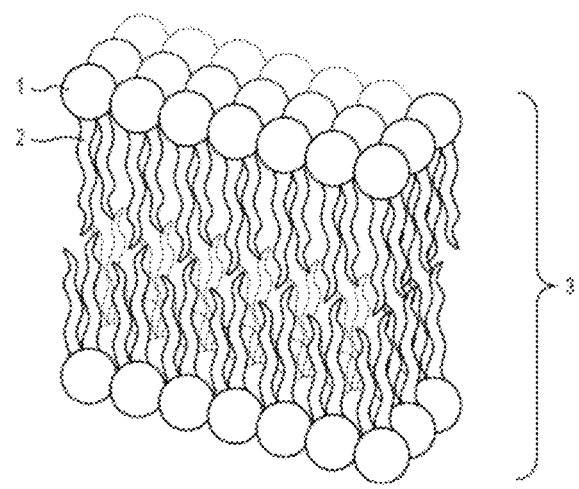
FIG. 1 is a schematic illustration of a phospholipid bilayer which may be present in embodiments of the present application.

The elastomeric article and methods of manufacture according to embodiments within the present application are described in further detail in this section.

Improving the Skin Care Properties of Elastomeric Articles

This application provides biologically enhanced protective elastomeric articles and methods for their manufacture. For the first time, there is provided an elastomeric article incorporating plant stem cell material. In preferred embodiments, the plant stem cells are derived from the apple plant, such as the species *Malus Domestica*. The plant stem cells can be immobilised on the elastomeric article through the use of a single-layer or bilayer membrane encapsulating system, for example liposomes, which are immobilised on the skin-contacting surface of the elastomeric articles to deliver authentic skin care properties. In alternative embodiments, liposomes or other bilayer membrane systems can be used to immobilise other skin care components for more effective delivery into the skin of the wearer.

The skin stem cells reside in the basal layer of epidermis and they continuously renew the skin cells. They remain dormant until they are activated by tissue injuries or skin diseases. Biological signals are received from the body to begin the repair mode, involving production of various proteins, carbohydrates and lipids to help wound repair, repair fine lines and wrinkles, maintain skin elasticity, and restore normal physiological functions and homeostasis of skin.

The long-term self-renewing stem cells start to degenerate as part of either the skin aging process, or induced by skin disorders and skin inflammation. This impairs stem cell mobilization and reduces the number of stem cells in the skin.

Plant stem cells contain epigenetic factors that have the potential to trigger cell signalling pathways to maintain the viability of human skin stem cells, thus providing various skin benefits. Benefits may include delaying skin senescence, aiding wound repair, aiding skin repair (following skin damage sustained through a disorder or injury), replacing dead skin cells due to apoptosis, protecting the skin barrier, maintaining skin elasticity through consistent collagen expression, aiding anti-inflammatory mechanisms, aiding skin antioxidant mechanisms and aiding skin detox systems. One or a combination of such benefits may be experienced. Skin protection and repair are the main target benefits. In embodiments of the invention, the plant stem cell material comprises epigenetic factors. In embodiments of the invention, the plant stem cell material contains DNA representative of the whole plant. This contrasts with any plant DNA that may be present in any other forms of plant extracts (other than plant stem cell lysates/extracts), which may contain a small amount of DNA associated with the component of the plant from which the extract is taken (e.g. the fruit of the plant, rather than the whole plant DNA complement.)

Glove coating technologies on the current market tend to be in the form of a coating of a substance, such as a simple plant material extract to provide an apparent moisturising effect to the skin, or a coating of a chemical substance that provides the effect of easy (slippery) donning. The simple plant extracts used on current gloves in the market are based on simple aqueous or organic extraction of a portion of the nutrients present in the plant, the composition of which can change markedly over the season and between different feed lots of the plant material. The extracts in use are not plant stem cell materials. Such simple extracts do not contain epigenetic factors, specifically plant epigenetic factors. In contrast, the plant stem cell material referred to in the present application contains epigenetic factors. Further, because the simple plant extracts are not coated onto gloves in a manner that provides protection to the plant extract nutrient components, there is potential deterioration of the plant extract composition on storage of the gloves.

Embodiments of the present application involve the use of a bilayer membrane system to encapsulate skin care components (which may be plant stem cell material, or any other skin care component such as a plant extract). The bilayer membrane system may be in the form of liposomes (or another of the enveloping structures described in detail below), or alternatively the bilayer membrane may have a different structure, as in the case of a bilayer membrane film (sheet-like or otherwise in shape). In the case of liposomes, the liposomes may be based on spherical phospholipid bilayer membranes that encapsulate and contain the aqueous and/or organic skin care component. In the case of a plant stem cell material in the form of a plant stem cell lysate containing aqueous and organic components, the liposomes contain aqueous components of the lysate within the aqueous centre of the liposome, and the organic components within the lipid bilayer wall. The liposomes (or other bilayer membrane systems) release the skin care components (active ingredients) upon contact with skin cell membrane. Liposomes have biocompatibility and can behave as a synthetic cell membrane, providing an artificial feel of skin cell-to-cell contact.

Embodiments of the present application implement the use of stem cell material, in particular stem cell epigenetic factors from a plant cell culture, encapsulated in a liposome system, followed by immobilization of the liposomes on the surface of elastomeric articles.

Plant Stem Cell Material

Plant stem cell material is a broad term that is used to encompass plant stem cells, lysates thereof, and extracts of plant stem cell cultures. Plant stem cells are plant-based stem cells, being cells which are capable of remaining in an undifferentiated state (e.g. totipotent, pluripotent or multipotent stem cells) for extended periods of time in culture until induced to differentiate into other cell types. The plant stem cells may be native or genetically modified, and are preferably native. In one embodiment, the plant stem cell material comprises plant stem cell epigenetic factors. The plant stem cell material may be in the form of the whole stem cell material—being substantially the entire contents of the lysed stem cells. To avoid doubt, it is noted that plant stem cell materials are multi-component mixtures containing multiple substances present in the relevant plant stem cells. The term "plant stem cell material" also does not encompass extracts of plant material (plant matter) into organic or aqueous solvents. Examples of such plant matter extracts include fruit extracts and juices, leaf extracts, bark extracts, root extracts, and whole plant extracts. Such plant extracts that are not plant stem cell extracts differ from plant stem cell extracts in terms of the DNA content (or epigenetic factor content), and the wider diversity in the components in the plant extracts. For example, fruit extracts will contain chemicals associated with the flavour and colour of the fruit, which are not present (or are not present at significant levels) in the plant stem cell material for the same fruit plant.

The plant stem cells are preferably dedifferentiated plant stem cells.

While in broad terms any plants may be used, in preferred embodiments, the plant is an apple or fruit belonging to the Rosaceae family, such as the Maloideae subfamily. Among the approximately 55 species of apple trees under this family, a preferred plant species is *Malus Domestica* or another Uttwiler Spatlauber apple tree. It is also possible to use other plant stem cells grouped under subkingdom Plantae in the production of gloves with a coating of plant stem cell material in accordance with other embodiments of the present application. Examples of plant species that may be used include apple varieties, grape varieties, Symphytum, alpine rose, argan trees, dwarf soapwort, tea plants under Family Theaceae, *Aloe Vera* under Family Asphodelaceae, *Citrus* under Family Rutaceae, *Cucumis* under Family Cucurbitaceae, Hibiscus under Family Malvaceae, *Lavandula* under Family Lamiaceae, *Calendula* under Family Asteraceae, Witch Hazel, Neem trees, Avocado trees and all other skin care plant derivatives under subkingdom Plantae and Kingdom Archaeplastida. Stem cells from Algae, particularly macro-algae and micro-algae, and more preferably green Algae, may be used.

A combination of two or more plant stem cell materials may be used. That is, plant stem cell material from two different species of plants may be used. As an example, a plant stem cell material from a plant of the Rosaceae family and from a plant of the Futaceae family could be selected. As another example, two different plant species both being from the Rosaceae family could be selected. Thus, throughout the specification, unless indicated to the contrary (for example, in Example 1 of the examples section where one plant stem cell material is specifically used), it should be understood that references to a plant stem cell material encompasses references to two or more plant stem cell materials.

The preferred plant species is *Malus Domestica*. Plant stem cells of *Malus Domestica* are totipotent. Where there is more than one plant stem cell material, the preferred plant species for at least one of these is *Malus Domestica*.

The stem cells of any of the selected plant species can be obtained from the cultivation of plant callus in vitro. Further details of suitable techniques for harvesting of plant stem cells are set out towards the end of the detailed description section below.

In embodiments, the epigenetic factors derived from the plant stem cells are used as the plant stem cell material. The epigenetic factors may be encapsulated into a liposome system as described in further detail below. Epigenetic factors are biological compounds that tag and interact with genetic material, namely nucleic acid, which change the phenotype but do not alter the genotype and the underlying nucleic acid sequence. Epigenetic factors act as biochemical tags that modulate gene expression for cellular function. Stem cell epigenetic factors are deoxyribonucleic acid (DNA) methylation, histone modification and micro ribonucleic acid (miRNA) bio-regulator proteins produced by totipotent biological building blocks for the maintenance of cell renewal, cell differentiation and cell pluripotency. In the case of *Malus Domestica*, this species of apple can be kept in storage for a relatively long period without withering, which may be a result of its stem cell epigenetic factors.

The plant stem cells of *Malus Domestica* have epigenetic factors which may assist in maintaining the stem cell characteristics "sternness" of the human skin stem cell. Human skin stem cell is a type of stem cell residing in the basal layer of skin epidermal which acts as a repair system to replace dead skin cells, and help maintain skin integrity and prevent premature skin aging.

Similar to mammalian stem cells, plant stem cell maintenance and fate is dependent on epigenetic factors. Plant stem cells of *Malus Domestica* in particular have protective properties on human stem cells, which includes (i) stimulating cell proliferation and (ii) improving viability in human stem cells. Human skin stem cells act as a repair system to restore dead cells due to apoptosis. Human skin stem cells are also responsible for the continuous skin renewal process to address injuries, skin disorders and dermatitis in order to maintain overall epidermal homeostasis and skin barrier protection.

Embodiments of the present application implement the use of plant stem cell material, in the form of a plant stem cell culture lysate, or an extract therefrom. It is to be noted that the extracts of plant matter, such as fruit extracts, leaf extracts, juices, bark or roots contain a wide variety of components, which vary over the course of the growing season. Plant stem cell materials, such as lysates, extracts and so forth, have a composition that does not vary over the course of a growing season, and with no (or minimal) components associated with the colour, flavour and so forth. The plant stem cell material contains a high concentration of plant stem cell dedifferentiated DNA matter (relative to plant matter extracts).

In embodiments of the invention, the plant stem cell material is not in the form of freeze dried plant stem cells. In preferred embodiments, the plant stem cell material, such as the lysate of plant stem cells, is incorporated into a bilayer membrane system to assist in delivery of the beneficial components to skin cells.

The plant stem cell material may be present on the surface of the elastomeric article in neat form (i.e. without encapsulation in a bilayer membrane, or without prior combination with a phospholipid). In alternative embodiments, the coating of plant stem cell material on the elastomeric film surface includes plant stem cell material and any other desired agents, such as film-forming agents, surfactants, emollients and so forth. Nevertheless, in preferred embodiments, the plant stem cell material is encapsulated in a bilayer membrane, or is combined with phospholipid, to aid in immobilisation on the elastomeric article surface and delivery of the beneficial components to the skin.

Bilayer Membrane Encapsulation Systems

Figure 2:
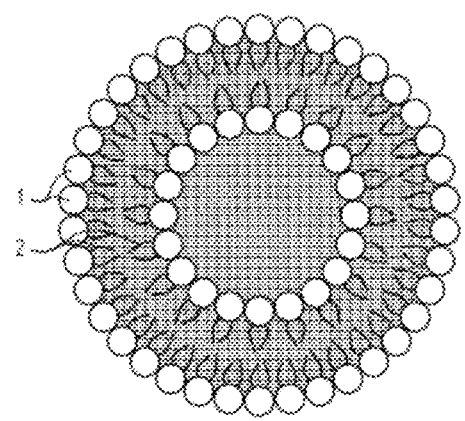
FIG. 2 is a schematic illustration of a liposome based on molecules having polar and non-polar ends, with the non-polar ends forming a non-polar bilayer, and containing a hydrophilic pocket, which may be a feature of embodiments of the present application.

Bilayer membrane systems are systems having a bilayer of molecules containing a polar or hydrophilic end, and a non-polar or hydrophobic end. The term "molecule" in this context extends to oligomers and polymers. The molecules used in the formation of bilayer membranes may be described as amphiphilic. Another description for suitable molecules for use in encapsulating the skin care component is lipid. The molecules are ordered into bilayers, which typically contain an ordered array of aligned molecules, in a two-layer arrangement. This is illustrated schematically in FIG. 1, where the following numerals indicate the following feature—(1) hydrophilic end (polar head group), (2) hydrophobic tail, (3) phospholipid bilayer. An example of a spherical (or liposome) form of bilayer membrane is illustrated in FIG. 2, in which the same reference numerals are used to indicate the same features.

Figure 3:
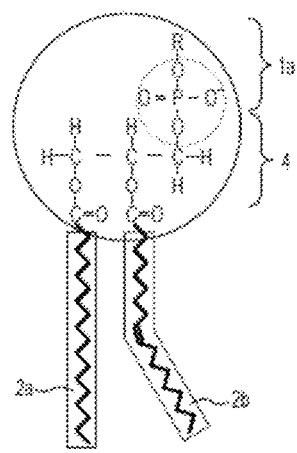
FIG. 3 is a schematic illustration of a phospholipid molecule that may be a feature of embodiments of the present application.

The bilayer membrane may be in any suitable form, encompassing liposomes, cerasomes, niosomes, transferosomes, ethosomes, cetosomes, cubosomes, sphingosomes, colloidosomes, aquasomes, and otherwise. Another form of encapsulating system that can be relied on is polymeric micelles. The molecules used to form the bilayer membrane may be organic or inorganic-organic hybrids. The molecules used to form the bilayer membrane contain a polar head group (1), a connector unit, and a hydrophobic tail (2), which may in fact be in the form of two hydrophobic tails. In the case of liposomes, these can be formed from lipid molecules, or lipid molecules coupled to other forms of molecules such as polymers. One suitable form of lipid molecule is that containing a phosphate (or modified phosphate) head group (1a), a glycerol-based connector unit (4), and two (saturated or unsaturated) fatty acid chains (2a) and (2b) (FIG. 3). The fatty acid chains may be saturated or unsaturated, and in typical examples may be of 10 to 22 carbon atoms in length (C10-C22). In the case of cerasomes, the polar head group may comprise a charged inorganic molecule (or polymer), a connector unit such as an amide, diamide, polyol (e.g. glycerol) or combinations thereof, and one or more fatty acid tails. The inorganic charged group may be a silyl group, such as an ethoxysilyl group, which may be formed into a siloxane network (or polymer). Liposomes and other phosphate-based bilayer membrane materials are preferred, so as to avoid the presence of silica in the elastomeric film product. Other bilayer membrane materials that may be used include ethosomes, niosomes, transfersomes, cetosome, aquasome, colloidosome, sphingosome, cubosome and the like.

In the following description, for simplicity, reference will be made to liposome forms of bilayer membrane systems, but it should be understood that the bilayer membrane material may be of another form as described above. In addition, reference will be made to the liposomes containing plant stem cell material, but as described elsewhere herein, the liposomes or other bilayer membrane systems may be used to encapsulate other skin care components for immobilization on the surface of the elastomeric film for delivery to the skin.

A liposome system is a spherical lipid bilayer of phospholipid and has been used in the past as a form of artificial cell (or synthetic cell, with a synthetic cell membrane based on the lipids). The lipid bilayer is able to fuse with human cell membrane and thus facilitate delivery of the encapsulated biological factors (e.g. plant stem cell material or other skin care components) to cells residing deeper in the skin. This is illustrated schematically in FIGS. 2 and 6.

A phospholipid (FIG. 2) is a molecule with two fatty acids (2a and 2b) and a modified phosphate group (1a) attached to a glycerol backbone (4). The phosphate may be modified by the addition of charged or polar chemical groups. Two examples of chemical groups that may modify the phosphate are choline and serine. The position of the modifying group is labelled R, via the hydroxyl group. Other examples of phospholipids may include the classes of phosphatidyl choline, phosphatidyl ethanolamine, phospholipid acid, phosphatidyl inositol, phosphatidyl glycerol, sphingomyelin and cardioplin, and mixtures of two or more thereof. Lecithin, which is a phosphatidylcholine, is a preferred phospholipid that may be used in the formation of the bilayer membrane encapsulating system in accordance with the present application.

As described above and as shown in FIGS. 1 and 3, phospholipids are amphipathic molecules that form lipid bilayers with the polar heads (1) of the molecules facing to the aqueous side and the fatty acid tails (2) projecting inwards and to the non-polar region. A spherical bilayer phospholipid forming a unilamellar liposome (FIG. 2) can be a model for an artificial cell membrane with its hydrophilic pocket containing various water soluble active ingredients, and the lipophilic or hydrophobic components.

Liposomal systems allow for the efficient entrapment of both hydrophilic and hydrophobic compounds. The liposomes may be anionic or cationic. Anionic liposomes are the subject of some embodiments of the present application. The lipid molecules may be derivatised if desired. In one example, the lipid molecules may be derivatised by polymers so as to form lipopolymers. Suitable examples include PEG. Such molecules are PEG-modified lipids. Linkage of the lipid to the polymer, or any other lipid-modifying group, may be via a carbamate linkage or otherwise.

Methods for the formation of the liposomes are described in detail further below.

The liposomes may be unilamellar or multilamellar. Liposomes can be classified into different size ranges, each of which can be used in the preparation of the elastomeric articles of the present application. These include small unilamellar vesicles having a size ranging from 20 nm-100 nm in diameter, large unilamellar vesicles (size range of 100 nm-400 nm in diameter), giant unilamellar vesicles (diameters≥1 μm) and large multilamellar vesicles (diameters 200 nm-3 μm). Small and large unilamellar vesicles are preferred for use in the products and methods of the present application. In some embodiments, the liposome diameter is from 20 nm to about 1000 nm, preferably 20 nm to 400 nm in size, or 20 nm to 100 nm in size. In other embodiments, the size range is from 200 nm to about 1000 nm, suitably 400 nm to 1000 nm. In the case of high pressure application during formation of the vesicles (liposomes or other vesicles), the size may be smaller, such as 1-10 nm.

Figure 4:
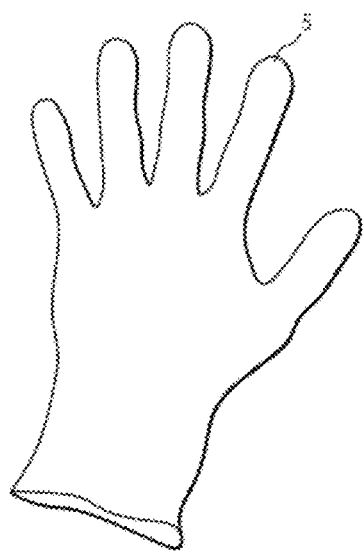
FIG. 4 is a schematic illustration of a glove, which is an example of an article within the scope of the present application.
Figure 5:
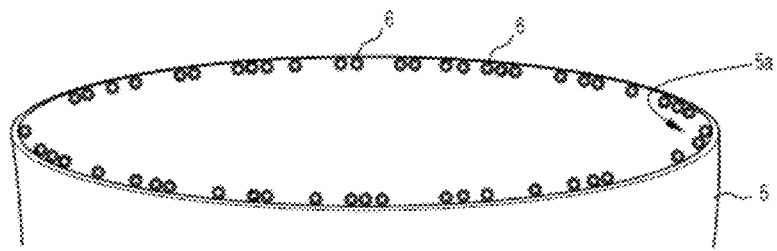
FIG. 5 is a schematic illustration showing (A) a cross-section of the glove of FIG. 4 in the cuff region, showing liposomes on the surface thereof in accordance with embodiments of the present application, and (B) an enlarged view of a portion of the glove cross-section (not to scale).
Figure 5:
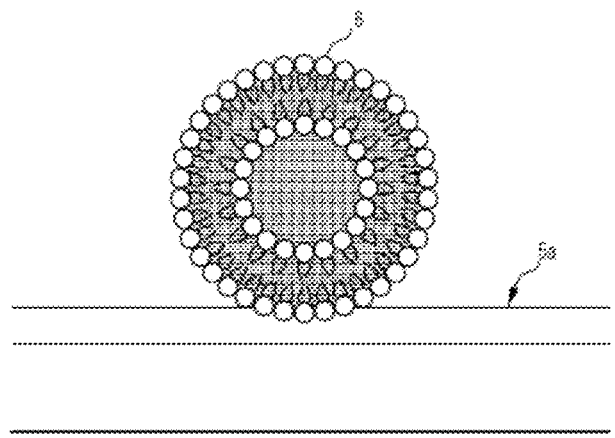
Figure 6:
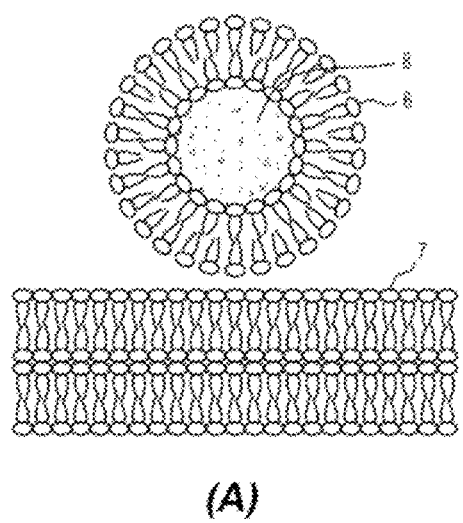
FIG. 6 is a schematic illustration showing (A) liposomes containing plant stem cell material approaching the skin cell membrane, and (B) a fusing of the liposomes with the skin cell membrane to release the liposomal contents.
Figure 6:
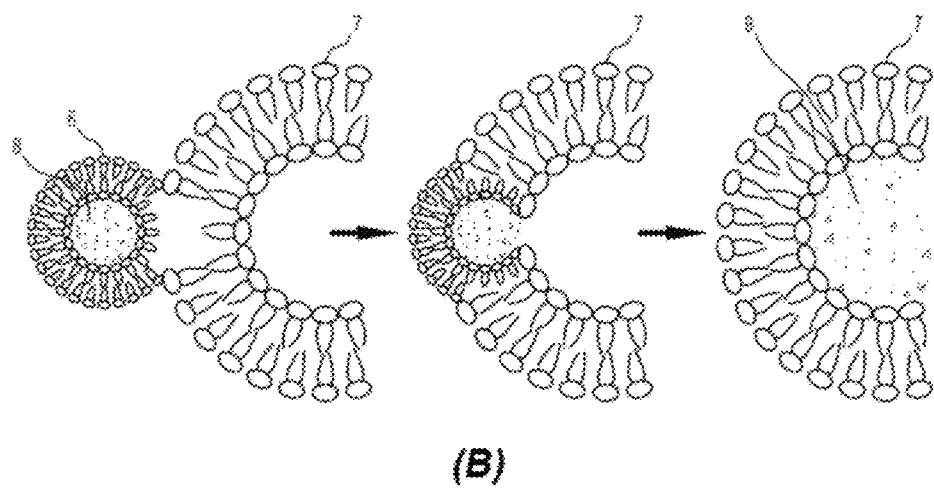

Suitable elastomeric products to which the present invention may be applied are gloves (5), an example of which is illustrated in FIG. 4. Another suitable form of article to which the present invention may be applied is condoms (not illustrated). *Malus Domestica* stem cell material encapsulated in liposomes (6) and immobilized on the inner surface (5a) of a glove, in accordance with an embodiment of the invention, is shown schematically in FIG. 5. The liposomes release the encapsulated epigenetic factors contained within the stem cell material upon contact with moist human skin via fusion of the liposomes and cell membrane (FIG. 6). As illustrated in FIG. 6 (parts (A) and (B)), whilst not wishing to be bound by theory, the applicant postulates that the liposomes (6) come into contact with the skin cell membrane (7), and then fuse with the cell membrane so as to release the stem cell material contents (8) of the liposomes into the cytoplasm of the contacted skin cells. This mechanism of delivery is the first of its kind in the field of elastomeric articles, especially gloves.

Liposomal plant stem cells are a preferred component of the elastomeric articles of the present application. Liposomal plant stem cells are not porous in the manner of porous beads containing impregnations of agents. Release of the liposomal contents is not via seeping from pores.

Alternative Encapsulating Systems

When the product of the present application includes a plant stem cell material, other encapsulating systems may be used in place of the bilayer membrane encapsulating system. Examples include microcapsules (see DE20100269 and U.S.

Pat. No. 7,988,983 for examples). Microcapsules may be based gelatin, shea butter gum, polyacetyl urea such as polyoxymethylene or combinations thereof. In such embodiments, the plant stem cell material is preferably encapsulated within the microcapsule, rather than being immobilised on a surface. Other forms of encapsulating systems may include micelles or other lipid or non-lipid based single-layer membrane systems, however bilayer membrane based systems are preferred.

Phospholipid-Based Coatings

In some embodiments, the elastomeric article is based on an elastomeric film, the plant stem cell material, and a phospholipid. The phospholipid may encapsulate the plant stem cell material, to thereby aid in immobilisation of the plant stem cell material on the film surface. The phospholipid is believed to provide some form of protection of the plant stem cell material during the manufacturing process. Depending on the conditions applied when combining the agents, the phospholipid may form micelles encapsulating part or all of the plant stem cell material components, or the phospholipid may form a bilayer membrane encapsulating part or all of the plant stem cell material components. It is also possible for an inverse arrangement of the bilayer to be formed, with a hydrophobic liquid medium surrounding the "inverse bilayer", a hydrophilic region between the bilayer of molecules, and a central hydrophobic zone. It is also possible for single-layer structures to be formed from the phospholipid molecules, containing a central hydrophilic region and a hydrophobic medium surrounding the micelles.

The phospholipid and plant stem cell material are combined together in a liquid medium, such as water, with any other desired components, to form a coating composition. This coating composition is applied to the film surface in accordance with the general procedures described in further detail below. The possible concentrations of components are also as outlined below. The presence of phospholipid on the film surface may be detected on the surface of an article following production using conventional analytical techniques.

Skin Care Component

In some alternative embodiments, the plant stem cell material may be substituted with another skin care component. Such skin care components or agents may be chosen for their positive effect on the skin, or for the sensation of a positive effect on the skin. To this end, the plant stem cell material referred to above, such as a plant stem cell lysate, may be considered to be an example of a skin care component. The plant stem cell lysate contains a range of components having skin care properties.

Thus, the present application also provides:
an elastomeric article comprising an elastomeric film and a bilayer membrane-encapsulated skin care component;
an elastomeric article comprising an elastomeric film, a skin care component, and a phospholipid for immobilisation of the skin care component on a surface of the elastomeric film;
a method for the manufacture of an elastomeric article comprising an elastomeric film having skin care properties, the method comprising immobilising a skin care component that is encapsulated by a bilayer membrane on a surface of the elastomeric film; and
a method for the manufacture of an elastomeric article comprising an elastomeric film having skin care properties, the method comprising applying a coating composition comprising a skin care component and a phospholipid onto a surface of the elastomeric film.

Other skin care components can be used instead of the plant stem cell material in embodiments of the invention that involve encapsulation in a bilayer membrane system. Examples of skin care components include essential oils, proteins, acids (including hyaluronic acid and other known acids having skin care properties), moisturizing materials, skin care agents, skin softening agents, skin renewal agents, fats, sun filters, antioxidants, immunity stimulation agents, vitamins (vitamins C and E as examples), lanolin and plant extracts (incorporating extracts or purified active agents derived from the plant or prepared synthetically, and including extracts of *Aloe vera*, fruits (including the fruits themselves, seeds, oils, or plant material from the fruit plant) vegetables and so forth), nuts, algae and so forth. Suitable plant or botanical extracts that may be used include grape seed extract, peppermint extract, camomile, *Aloe vera*, Jojoba, Aloe barfadenis extract, passion flower extract, cucumber extract, comfrey leaf extract, saponaria, officinalis extract, myrrh extract, eucalyptus extract, ginseng extract, algae extract, seaweed extracts and combinations thereof. Preferred skin care components are selected from plant and botanical extracts. Any other components may be combined with the skin care component as desired. These may include proteins, peptides, hormones, antibodies, growth factors, vitamins, genetic materials, bird nest extract and pharmaceutical agents (drugs). These may have skin care qualities or otherwise.

As far as the combination of skin care component (including plant stem cell material in particular) and bilayer membrane-forming materials (such as phospholipid) are concerned, the relative amount of total skin care components to bilayer membrane-forming material (e.g. phospholipid) may be from 0.001% to 80% by weight of the combination. The bilayer-membrane-forming material, such as phospholipid, may constitute from 20% to 99.99% by weight of the combination. The amount of the skin care component may be at least 0.1%, 1%, 5%, 10%, 20%, 30%, 40% or at least 50% by weight of the total combination (of skin care component and bilayer membrane-forming material such as phospholipid). The amount of phospholipid (or other amphiphilic material) may be at least 20%, 30%, 40%, 50% or 60% of the combination. In the example of liposomal plant stem cell material formed from a lipid and lysed plant stem cells, it is taken that the entire plant stem cell material constitutes a skin care component, and this constitutes the entirety of the material encapsulated by the bilayer membrane. In other examples, it is possible to combine a plant stem cell material (component "A") with another type of skin care component (e.g. a botanical extract, vitamin, etc—referred to as component "B"). The amounts for the skin care component referred to above refer to the total of A and B, with the balance ("C") being for the phospholipid or other amphiphilic molecule. The amount of plant stem cell material can be combined with other components to reduce the relative amount of that component to reduce costs.

Components A, B and C are typically combined with other components in the coating composition, such as water or another liquid medium, glycerol, thickeners (e.g. gums), preservatives (e.g. phenoxyethanol) and antioxidants. Varying the amounts of these components can also reduce the amount of plant stem cell material that is present in the coating composition, to achieve a suitable balance between efficacy and cost. Some of these components, such as the liquid medium/water, may be removed on drying of the coating composition, leaving behind other coating composition components on the film surface, including the plant stem cell material or other skin care component.

Where the skin care component is a plant stem cell material, the amount of plant stem cell material on the surface of the elastomeric film of the elastomeric article may be between 0.0001% and 50% by weight of the article. In this case, it is noted that the plant stem cell material may constitute the entirety of the composition applied to the surface of the elastomeric film, or may constitute one of the components of a multi-component composition applied to the surface of the elastomeric film. The other components of the multi-component composition may include the liposomal material (such as the amphipathic molecules, for example the phospholipid material). Water may be another component of the composition applied to the surface of the elastomeric film during production, and may be partially, substantially or completely removed during drying. When determining the amount of plant stem cell material as a percentage by weight of the final article, account is made of the other components applied, and the loss of water or other solvent.

Amounts of Components

The amount of plant stem cell material may in some embodiments be at least 0.0001%, 0.0005%, 0.001%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39% or 0.4% by weight of the elastomeric article. The amount of plant stem cell material may in some embodiments be not more than 50%, 40%, 30%, 20%, 10%, 5%, 4.5%, 4%, 3.5%, 3%, 2.5%, 2%, 1.5%, 1%, 0.5%, 0.45%, 0.4%, 0.35%, 0.2%, 0.19%, 0.18%, 0.17%, 0.16%, 0.15%, 0.14%, 0.13%, 0.12%, 0.11%, 0.1%, 0.09%, 0.08%, 0.07%, 0.06%, 0.05%, 0.04%, 0.03%, 0.02%, 0.01%, 0.009%, 0.008%, 0.007%, 0.006% or 0.005% by weight of the elastomeric article. Any lower and upper limit can be combined together for a suitable range, the only limitation being that the lower limit must be below the upper limit. Thus, suitable ranges for the amount of plant stem cell material may be between 0.001% and 0.005%, or between 0.1% and 0.18%, and so forth. Higher amounts may be suited to low weight articles such as condoms, where the coating composition may constitute a significant proportion of the weight of the condom. In view of the light weight of thin film gloves too, the coating composition may constitute a significant amount of the total weight of the article.

The amount of bilayer membrane-encapsulated skin care component (including in particular the bilayer membrane-encapsulated plant stem cell material) on the surface of the elastomeric film of the elastomeric article may be between 0.0001% and 80% by weight of the total weight of the elastomeric article. In this case, it is noted that the bilayer membrane-encapsulated skin care component may constitute the entirety of the (dried)coating layer applied to the surface of the elastomeric film, or may constitute one of the components of a multi-component composition applied to the surface of the elastomeric film. In some embodiments, the bilayer membrane-encapsulated skin care component is applied as an aqueous suspension. The bilayer membrane-encapsulated skin care component includes the components of the membrane-forming molecules (e.g. the phospholipid material) and the skin care component (e.g. the plant stem cells). Where the bilayer membrane-encapsulated skin care component constitutes the entirety (or substantially the entirety) of the coating composition (other than water that is removed following application), the % by weight contribution of this composition to the final product can be calculated by comparing the coating-free elastomeric article to the final product containing the immobilized bilayer membrane-encapsulated skin care component on its surface (i.e. at the end of the manufacturing process, and in the dried form). The increase in weight from the pre-coated to the post-coated product can be attributed to the bilayer membrane-encapsulated skin care component. Where other components that are not evaporated from the coating composition during drying are present, a percentage attributable to each component can be calculated. The bilayer membrane-encapsulated skin care component preferably constitutes at least 50%, at least 60%, at least 70%, at least 80% or at least 90% of the (dried) coating on the elastomeric article. However, in some embodiments (for example, to minimize the cost of the article that is attributed to the more expensive bilayer membrane-encapsulated skin care component) the bilayer membrane-encapsulated skin care component may constitute as little as 1% of the (dried) coating, or at least 5%, 10%, 20%, 30% or 40% of the (dried) coating.

The amount of bilayer membrane-encapsulated skin care component (i.e. the whole combination) may in some embodiments be at least 0.0001%, 0.01%, 0.02%, 0.03%, 0.04%, 0.05%, 0.06%, 0.07%, 0.08%, 0.09%, 0.1%, 0.5%, 1%, 1.5%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 10%, 20%, 30% or 50% by weight of the total weight of the elastomeric article. The amount of bilayer membrane-encapsulated skin care component may in some embodiments be not more than 80%, 50%, 40%, 30%, 20%, 10%, 5%, 4.5%, 4%, 3.5%, 3%, 2.5%, 2%, 1.5%, 1%, 0.5%, 0.2%, 0.15%, 0.1%, 0.09%, 0.08%, 0.07%, 0.06%, 0.05%, 0.04%, 0.03% or 0.02% by weight of the total weight of the elastomeric article. Any lower and upper limit can be combined together for a suitable range, the only limitation being that the lower limit must be below the upper limit. Thus, suitable ranges for the amount of bilayer membrane-encapsulated skin care component may be between 0.01% and 0.05%, or between 1% and 4%, and so forth.

In the case of articles containing a coating based on skin care component (i.e. plant stem cell material in particular) and phospholipid, the amount of the combination of skin care component and phospholipid, as a percentage of the total weight of the elastomeric article, may be at least 0.0001%, 0.01%, 0.02%, 0.03%, 0.04%, 0.05%, 0.06%, 0.07%, 0.08%, 0.09%, 0.1%, 0.5%, 1%, 1.5%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 10%, 20%, 30% or 50% by weight of the total weight of the elastomeric article. The amount of skin care component and phospholipid in various embodiments is not more than 80%, 50%, 40%, 30%, 20%, 10%, 5%, 4.5%, 4%, 3.5%, 3%, 2.5%, 2%, 1.5%, 1%, 0.5%, 0.2%, 0.15%, 0.1%, 0.09%, 0.08%, 0.07%, 0.06%, 0.05%, 0.04%, 0.03% or 0.02% by weight of the total weight of the elastomeric article. Any lower and upper limit can be combined together for a suitable range, the only limitation being that the lower limit must be below the upper limit. The amount of skin care component to phospholipid is typically around 1:99 to 80:20, such as between 10:90 to 80:20 or 10:90 to 60:40.

The total weight of the (dried) coating (i.e. following removal of water) may be between 0.0001 and 80% by weight of the elastomeric article. The minimum amount may be any of the minimums indicated above for the bilayer membrane-encapsulated skin care component (i.e. plant stem cell material), and the maximum may be any of the maximum amounts indicated for the bilayer membrane-encapsulated skin care component.

In the example of a glove, weighing approximately 4 g (prior to coating), the coating composition may be applied in a typical amount of between 4 mg to 100 mg, equivalent to 0.1% to 2.5% by weight of the article weight. The plant stem cell material may constitute around 10% to 50% by weight of the coating composition (i.e. dried form), in typical embodiments. Thus, a typical % amount of plant stem cell material per glove may be in the region of 0.01% to 1.25% by weight of the article. In the case of condoms, a typical weight of the uncoated condom may be around 100 mg-300 mg, and a suitable coating weight for application to the condom may be around 10 mg to 150 mg. This is equivalent to a (dried) coating amount (as a percentage by weight of the total article weight) of 9% to 33%. Based on about 10% to 50% plant stem cell material in the coating composition, the overall amount of plant stem cell material per article in this case would be around 1% to about 17% by weight of the total article. These amounts also serve as a useful guide to a range of other articles, although the amounts may be higher. In the case of coverings for the skin (e.g. face masks), a thicker coating layer, containing or consisting of plant stem cell material, may be desired. The applied layer may even be heavier than the elastomeric film component. In such cases, the dried coating layer may constitute from 10% to 80% of the total weight of the article. The plant stem cell material may constitute from 10% to 80% by weight of the total weight of the article.

Immobilisation of the plant stem cells on the elastomeric film can be achieved by any of a range of techniques. One preferred technique involves encapsulation in a bilayer membrane system, such as liposomes. The liposomes may then be immobilised on the elastomeric film surface through ionic interactions or ionic reactions between the liposomes and the surface groups on the elastomeric film. Similarly, in the case of other bilayer membranes containing plant stem cell material or other skin care components, there may be an ionic interaction or ionic reaction causing the bilayer membrane encapsulation system to be immobilised on the surface of the elastomeric film. The ionic interaction or reaction may be via the polar head groups of the amphiphilic molecules and ionic surface groups at the surface of the elastomeric film. There may additionally or alternatively be hydrogen bonding involved through the polar head group of the amphiphilic molecule.

The plant stem cells, such as bilayer film-encapsulated plant stem cell material, may be present as a coating on a surface of the elastomeric article. The combination of plant stem cell material and phospholipid may similarly be present as a coating on a surface of the elastomeric article. The coating is preferably on the surface of the article that comes into contact with the skin. For example, in the case of a glove, the coating is preferably on the inner surface of the glove. This is illustrated schematically in FIG. 5, with part (A) illustrating a cross-section at a wrist section of the glove (towards the finger end of the wrist), and part (B) illustrating liposomes containing stem cell material immobilised on an inner surface of the glove. The inner surface is the surface of the glove that comes into contact with the wearer of the glove.

Other Coating Components and Variations

The plant stem cell material may be applied as a component of a coating composition on a surface of the elastomeric article. In this section some additional features of such coating compositions are described. Techniques for forming the coating on the elastomeric article are described in a separate section following description of the formation of the elastomeric article—that section includes additional information on possible coating composition features.

The amount of plant stem cell material, or coating composition, may be between 0.0001 and 50% by weight of the article. In the case of gloves, the amount may be between 0.004 and 2000 mg/glove, preferably 0.5-1.5 mg/glove. This amount is based on a typical size of 6-8 glove, or a glove of about 4 grams in weight.

The plant stem cell material, whether alone or in the form of liposomes or combined with phospholipid, may be combined with other coating components including hydrogels, elastomers, bio-polymers, bio-sealants, preservatives, stabilisers, emulsifiers, pH stabilisers, anti-ozonants, waxes, wetting agents, thickeners and the like.

In some embodiments, the coating components, or the coating composition, is wax-free. In some embodiments, the coating composition is an aqueous composition, and thus free of organic solvents. In other embodiments, the coating composition contains water and/or a non-flammable organic solvent as the liquid phase for delivery of the coating components to the surface of the elastomeric film. For example, the liquid phase, which is evaporated on drying of the coating, may be water and/or a non-flammable alchohol. In some embodiments, the coating components, or the coating composition, is free of oils. In some embodiments, the coating on the elastomeric article is non-oily, and does not have an oily feel to touch.

In some embodiments, the coating composition containing the plant stem cell material is free of elastomers. It is generally intended that the coating composition containing the plant stem cell material is not an elastomeric film composition coating.

In other embodiments, the coating composition contains elastomer. In such embodiments, the amount of elastomer is preferably not more than 10% by weight of the dried coating. The ratio of elastomer to plant stem cell material may vary widely within such coating compositions, and could be around 99:1 elastomer:skin care component or higher (e.g. containing trace skin care component) or lower (e.g. 1:99), as examples. Having a small amount of elastomer in the coating composition may aid in immobilisation of the plant stem cell material onto the article surface.

The coating (that is, the skin care composition coating) may contain a hydrogel component. Where there is a bilayer membrane-encapsulating system in the form of a liposome system, the hydrogel may be additional to this. The hydrogel may be intimately combined with the plant stem cell material, for combined coating, or it may form a separate layer. In the case of a combined coating, the amount of hydrogel is preferably between 0.001% and 50% by dry weight of the coating composition, and preferably between 0.1 and 20% of the total weight of the coating composition (including water). In the case of a combined coating, the hydrogel may aid in release of plant stem cell material, or liposomal plant stem cell material, through swelling and consequent release of liposomes from the article surface. It is also possible to rely on hydrogel interlinking with the liposomal plant stem cells as the immobilization coating.

Suitable hydrogels may include those described in US20050132466 and US20050222543. Suitable hydrogels may include propenoic acid-based hydrogels, polyacrylic based hydrogels, polyacrylamide hydrogels, silicon-based hydrogels, starch, alginate, agarose and encompassing groups of homopolymeric hydrogels, copolymeric hydrogels and multipolymer interpenetrating polymeric hydrogel. Suitable hydrogels may allow for resilient stretching of the underlying elastomeric film to occur without disturbance of the hydrogel coating. Hydrogels having an elongation at break of greater than 200% are preferred.

In some embodiments, a separate immobilization coating may be present between the elastomeric film layer and the coating of the plant stem cell material. The separate immobilization coating may be based on a hydrogel or otherwise.

The skin care composition coating may contain any other desired ingredients. Such ingredients may include anti-tacking agents, antimicrobial agents, moisturizing active ingredients, antioxidants, silicon emulsions and/or skin care active ingredients. One example is coenzyme-Q10. In this context, the other ingredients form part of the coating composition and are not encapsulated by the bilayer membrane. However, it is noted that elsewhere in this specification the possible inclusion of such components as encapsulated components is described.

The skin care coating on the final elastomeric article (following drying) may in some embodiments contain at least 50% plant stem cell extract, as a percentage of the total (dried) coating. In some embodiments, the amount of plant cell extract in the skin care coating is at least 60%, 70% or 80% of the composition.

The skin care coating on the final elastomeric article (following drying) may in some embodiments contain at least 50% of a bilayer membrane-encapsulated skin care component, as a percentage of the total (dried) coating. In some embodiments, this is a bilayer membrane-encapsulated plant stem cell material. In some embodiments, the amount bilayer membrane-encapsulated skin care component in the skin care coating is at least 60%, 70% or 80% of the composition.

Elastomeric Articles

Examples of elastomeric articles that benefit from having skin care properties include gloves (encompassing disposable gloves, surgical gloves, examination gloves, industrial gloves, laboratory gloves, irradiation gloves, industrial gloves, clean room gloves for electronic industries, gloves for food contact and food processing and biotechnical application, household gloves and so forth), finger cots, condoms, coverings intended for contact with skin (including protective coverings intended for contact with skin and therapeutic coverings intended for contact with the skin such as face mask sheets—which may deliver the skin care component coating to the skin of the wearer) and the like. The articles are suitably disposable elastomeric articles—being of light weight and low cost, suitable for disposable after a period of use. The articles may be thin film articles. The articles may be described as barrier film articles. Barrier film articles are substantially free of pores so as to prevent the transmission of fluids across the film. The film is a continuous film. The films are therefore to be contrasted with fabrics or webs formed from woven elastomeric strands with pores between the strands. The articles may be dipped articles (i.e. articles produced from a dipped elastomeric film, noting that the skin care composition may be applied by dipping or otherwise). The articles may comprise a single layer film, or a multilayered film, plus the skin care composition coating. Other coatings such as slip coatings or powder coatings to aid donning may also be present, but in some embodiments, the articles consist of the elastomeric film and the skin care coating as described herein.

The thickness of the elastomeric film (including the skin care composition/coating) can, for example, be in the range 0.01-3.0 mm, such as 0.01-0.3 mm, 0.02-0.2 mm, 0.05-0.10 mm, 0.03-0.08 mm, or 0.05-0.08 mm (for thin or disposable gloves and articles), and 0.2-3.0 mm for thick gloves. The thickness is suitably measured as an "average thickness" for the article. In the case of gloves, the thickness is measured using an average of the thickness measurements taken at the three points described below. In some embodiments, the film thickness of a glove is less than 2 mm (e.g. from 0.01 mm to 2 mm). For example, the film thickness may be in the range of from 0.04 mm to 2 mm. In another embodiment, the glove may have a weight of about 4 grams, or about 3 grams, while it will be appreciated that higher and lower glove weights may also be obtained depending on the purpose for which the glove is to be used.

The elastomeric film of the article may contain one layer or be made from multiple layers produced by subsequent dipping steps. For example, the final film (or article) may comprise from 1 to 15 layers. In some embodiments, there is a single elastomeric film layer, in other embodiments there are 1, 2 or 3 elastomeric film layers. In some embodiments, there are 2 or 3 elastomeric film layers.

The elastomeric articles as described herein retain the desirable elastomeric properties of the underlying elastomeric films, in spite of the addition of the skin care composition or coating. Thus, articles can be produced containing a modulus at 500% of less than 15 MPa. The articles can contain an elongation at break of at least 500%. The articles can have these properties combined.

Elastomers

Elastomer-forming polymers include natural rubber and synthetic elastomer-forming polymers, which can be cross-linked to produce elastomeric films. The polymer may be a single polymer or a combination of two or more polymers. The polymer may be a homopolymer or a copolymer, or a blend of polymers/copolymers.

The synthetic elastomer-forming polymer may be a polymer containing free ionically cross-linkable groups, covalently cross-linkable groups, or a combination of both. Examples of ionically cross-linkable groups are acids, including carboxylates, sulfonates and acid anhydrides, and an example of a covalently cross-linkable group is a double bond.

The elastomer-forming polymers may be selected from rubber (natural or synthetic), nitrile rubber, polyurethane, polyisoprene, polychloroprene, acrylic polymers (including acrylic diene block copolymers), polybutadienes, copolymers of these and other polymers/monomers (random copolymers, block copolymers or otherwise) and modified forms of these polymers or copolymers (e.g. polymers containing additional substituents such as carbon/late, sulfonate, halide or other substituents).

Synthetic elastomer-forming polymers include copolymers produced by copolymerisation of conjugated diene monomers and ethylenically unsaturated acid monomers (carboxylated polyacrylonitrile butadiene being an example of such a copolymer), polyisoprene, polychloroprene, styrene copolymers and/or polyurethane. Amongst the range of conjugated diene monomers, examples are 1,3-butadiene, iso-prene, 2,3-dimethyl-1,3-butadiene, 2-ethyl-1,3-butadiene, 1,3-pentadiene, chloroprene and acrylonitrile. Regarding ethylenically unsaturated acid monomers, the acid group may be a carboxyl group, a sulfonic acid group or an acid anhydride group. Examples of ethylenically unsaturated acid monomers include acrylic acid or methacrylic acid; itaconic acid, maleic acid, fumaric acid, maleic anhydride, citraconic anhydride, sytrenesulfonic acid, monobutyl fumarate, monobutyl maleate, mono-2-hydroxypropyl maleate, and alkali metal or ammonium salts thereof. The polymers used may be carboxylated or non-carboxylated, as desired.

One notable example of a synthetic elastomer-forming polymer is polyacryonitrile butadiene. This may be carboxylated or non-carboxylated. This may be provided as a mixture of carboxylated nitrile latex and nitrile butadiene rubber.

Carboxylated refers to the presence of carboxylate (carboxylic acid or ester) groups on the polymer chain. Carboxylation may be achieved by forming the polymer with a monomer containing carboxylate groups, or through grafting carboxylate groups to a polymer. As examples of suitable carboxylated polymers, reference is made to PCT/AU2014/000726 and PCT/AU2014/000727, the entirety of each being incorporated into this specification by reference. The degree of carboxylation may be between 5-15% (or 5-10%).

In the art of the present invention, it is common to refer to the amount of the elastomer-forming polymer as being 100 phr (per hundred parts "rubber"), and for the relative amounts of the remaining components of a composition for producing an elastomeric film to be calculated as a number of parts compared to the 100 phr of the elastomer-forming polymer, by weight. Thus, for an amount of cross-linking agent that is 1/100th that of the elastomer-forming polymer in the composition by weight, the amount of cross-linking agent is referred to as 1.0 phr.

Other Components used to Produce the Elastomeric Film

Elastomer-forming polymers can be cross-linked with one or more cross-linking agents to produce the elastomeric film. Various types of cross-linking agents can be used. Other agents that may be present in the composition used to produce the elastomeric film-forming composition include plasticizers, anti-ozonants, stabilisers such as pH stabilisers, surfactants, emulsifiers, antioxidants, vulcanising agents, polymerisation initiators, pigments, fillers, colourising agents and sensitisers. Many of these agents are added in particulate form. Others are added as liquids. These are added prior to forming the latex composition into the shape of the synthetic elastomeric article. In some embodiments they are added at the same time as the cross-linking agent. In other embodiments, they are added after.

Cross-Linking Agents

Cross-linking agent classes include ionic cross-linking agents and covalent cross-linking agents. The cross-linking agent or agents used in the production of the elastomeric film may be selected from ionic cross-linking agents, covalent cross-linking agents, and combinations thereof. The selection will depend on various factors including the properties of the film desired and the choice of elastomer.

Ionic cross-linking agents include metal oxide cross linking agents (such as zinc oxide and magnesium oxide), peroxides (such as 1,1-di(t-butylperoxy)-3,3,5-trimethylcyclohexane, which can be purchased under the trade name Trigonox 29-40B-pd) and solubilized ionic cross-linking agents such as solubilised sodium aluminate. Other ionic cross-linking agents amongst those known in the art and be used. These include the cross-linking agents described in PCT/AU2016/050308, PCT/AU2016/050311 and PCT/AU2016/050312, the entirety of each being incorporated by reference.

Covalent cross-linking agents include organic cross-linking agents, sulphur and/or sulphur donors, and combinations thereof.

Suphur may be added in the form of elemental sulphur. Sulphur donors are another way of providing sulphur cross-linking. Sulphur donors release sulphur, or act with sulphur-containing compounds, to accelerate sulphur-based covalent cross-linking of the elastomer-forming polymer. Generally, sulphur donors can be advantageous as they shorten the curing (vulcanisation) time, lower the curing temperature or decrease the amount of cross-linking agents required to be used in the composition. However, on the negative side, sulphur donors can give rise to allergic reactions, such as allergic contact dermatitis with symptoms including erythema, vesicles, papules, pruritus, blisters and/or crusting. Examples of suitable sulphur donors include the carbamates such as thiocarbamates (e.g. zinc dibutyl dithiocarbamate (ZDBC), Zinc diethyl dithiocarbamate (ZDEC); Zinc dimethyl dithiocarbamate (ZDMC); thiurams (e.g. tetraethylthiuram disulfide (TETD), Tetramethylthiuram disulphide (TMTD)); Dipentamethylene thiuram tetrasulfide (DPTT); Dipentamethylene thiuram hexasulfide (DPTH); Dipentamethylene thiuram hexasulfide; thiourea (Ethyl thiourea (ETU) and diphenylthiourea (DPTU); thiazoles (e.g. Mercapto Benzothiazoles (MBT), Mercapto Benzothiozole disulphide (MBTS), zinc 2-mercaptobenzothiazole (ZMBT)); guanidines (eg. Diphenylguanidine (DPG)) and aldehyde/amine-based sulphur donors (eg. hexamethylenetetramine). Other examples are well known in the art and can be obtained from various publicly available sources.

Other cross-linking agents that may be used can be selected from, but are not restricted to, crosslinking monomers, reactive oligomers, polyisocyanate oligomers, functional crosslinkable polymers, derivatives of ethylene glycol di(meth)acrylate (such as ethylene glycol diacrylate, di(ethylene glycol) diacrylate, tetra(methylene/ethylene glycol) diacrylate, ethylene glycol dimethacrylate (EDMA), di(ethylene glycol) dimethacrylate (DEDMA), tri(methylene/ethylene glycol) dimethacrylate, tetraethylene glycol dimethacrlate (TEDMA)), derivatives of methylenebisacrylamide (such as N,N-methylenebisacrylamide, N,N-methylenebisacrylamide, N,N-(1,2 dihydroxyethylene)bisacrylamide), formaldehyde-free crosslinking agents (such as N-(1-Hydroxy-2,2-dimethoxyethyl)acrylamide), divinylbenzene, divinylether, diallyl phthalate, divinylsulfone, Trimethylolpropane Trimethacrylate (TMPTMA), polyfunctional crosslinkers and the like. Some of these cross-linking agents are commercially available and are supplied by companies such as Aldrich. Combinations of these cross-linking agents can also be used.

In broad terms, any amount of cross-linker may be used, as required for the final article properties. Thus, the total amount of cross-linking agents in the composition may be between 0.01 and 14 phr. However, it is usually desirable to minimise cross-linker amounts (and the associated costs or disadvantages). The total cross-linking agent amount may be within one of the following ranges: 0.01-14.5 phr, 0.2-12.5 phr, 0.3-10 phr, 0.1-10 phr, 0.2-10 phr, 0.3-9 phr, 0.5-9 phr, 0.8-9 phr, 0.3-8 phr, 0.5-8 phr, 0.8-6 phr, 1-5 phr, 2-9 phr, 3-10 phr, 3-7 phr, 1-3 phr, 0.01-0.5 phr, 0.01-1.0 phr.

The amount of ionic cross-linking agent may be between 0.0-4.0 phr, such as 0.01-4.0. The amount is preferably lower still, at 0.01-3.0 phr, or 0.01-2.0 phr, 0.01-1.0 phr or 0.01-0.5 phr.

The amount of sulphur may be between 0.0-5.5 phr. The amount may be lower still, at 0.0-3.5 phr, such as 0.01-3.0 phr, 0.01-2.0 phr, 0.01-1.5 phr, 0.01-1.0 phr or 0.01-0.5 phr.

The amount of sulphur donor may be between 0.0-2.0 phr, such as between 0.1-1.5 phr, 0.1-1.0 phr, 0.2-1.0 phr, 0.3-2.0 phr, 0.3-1.5 phr or 0.2-0.6 phr.

The amount of organic cross-linking agent may be between 0.0-4.0 phr, such as 0.01-4.0 phr. The amount may be lower still, at 0.01-3.0 phr, or 0.01-2.0 phr, or 0.01-1.0 phr.

The cross-linking agent can be combined with the latex composition and other components of the elastomeric film-forming composition at suitable time points for the formation of the desired type of film. Cross-linking agents are typically added to the latex composition with other components, however for some forms of cross-linking agent (such as the solubilised ionic cross-linking agents, including sodium aluminate) there is a preliminary step involving the formation of a cross-linking composition and combining this with the latex under controlled conditions, followed by the addition of other components and secondary cross-linking agents.

Other Components of the Elastomer Article-Forming Compositions

Stabilisers may be used in the elastomeric article-forming composition. The stabilizer may be, for example, an anionic surfactant and or other non-ionic surfactants. The elastomer-forming polymer can be diluted with a solution of a stabilizer, such as potassium hydroxide, ammonium hydroxide and/or sodium hydroxide. The amount of stabiliser used is dependent on the polymer used in the elastomeric film-forming composition, the pH of the composition and other factors. The stabiliser can range from 0.1-5.0 phr, e.g. 0.5 to 2 phr, preferably 1.0 to 1.5 phr, which is diluted with water, preferably filtered water-or de-ionized water, or water having a total solid content of around 5 ppm level.

One form of stabiliser that may be used in the composition is a mechanical stabiliser. Such stabilisers aid in maintaining the stability of the latex composition, particularly when there is a solubilised component (such as solubilised ionic cross-linking agent), by providing structural support around the ions to avoid re-precipitation or re-crystallisation. The mechanical stabiliser may be a water-miscible or water-soluble organic polyol, or a water-soluble or water-miscible thickening agent, examples of which are well known in food or pharmaceutical manufacture. Examples of such polyols and thickeners include glycerine, sugars and sugar alcohols, maltodextrin, polysaccharide, polyglycerol, polyethylene glycols, starch, modified starch, and mixtures thereof.

Emulsifiers may be used in the elastomeric article-forming composition. Suitable emulsifiers include sodium alkyl aryl sulphates, sodium alkyl sulphates or other anionic/non-ionic surfactants. The amount of emulsifier used is dependent on the polymer used in the elastomeric film-forming composition, the pH of the composition and other factors. The amount of emulsifier can range from about 0.1 to 3 phr.

pH stabilisers may be used to avoid the possibility of destabilization, which is possible where the polymer contains carboxylic acid groups. Suitable pH stabilisers include potassium hydroxide, ammonium hydroxide and/or sodium hydroxide. Preferably, the pH stabiliser is potassium hydroxide. A diluted stabilizer solution can be mixed with the polymer. The pH of the mixture is suitably adjusted to between about 8.5 to about 12.5, or between about 8.5 to about 11.0. The cross-linking agent(s) can then be added to the mixture.

Anti-ozonants may be used in the elastomeric article-forming composition. Suitable anti-ozonants include paraffinic waxes, microcrystalline waxes and intermediate types (which are blends of both paraffinic and microcrystalline waxes). The amount of anti-ozonant can range from about 0.0 to 5.0 phr.

Antioxidants may be added to the elastomeric article-forming composition of the present invention. Suitable antioxidants include hindered arylamines or polymeric hindered phenols, and Wingstay L (the product of p-cresol and dicyclopentadiene). The antioxidant may, for example, be added in an amount ranging from 0.0-5.0 phr, 0.0-3.0 phr, 0.0-1.0 phr or 0.3-0.5 phr.

Pigments such as titanium dioxide, selected for its pigmentation, to reduce the transparency of the final elastomeric film, may be added in amounts ranging from 0.01-10.0 phr, such as 1.5-2.0 phr or 1.0-3.0 phr and colorants can also be added in the desired amounts. The mixture is then diluted to the target total solids concentration by the addition of a liquid, such as water. The pigments used in the elastomeric film-forming composition may be selected from the group consisting of EN/USFDA approved dyes.

Rubber reoderants may be used in the elastomeric article-forming composition. Suitable rubber reoderants include perfume oils of natural or synthetic origins. The amount of rubber reoderant can range from about 0.001 to 2.0 phr.

Wetting agents may be used in the elastomeric article-forming composition. Suitable wetting agent emulsifiers include anionic surfactants like sodium dodecyl benzene sulfonate or sodium lauryl ether sulfate, or non-ionic ethoxylated alkyl phenols such as octylphenoxy polyethoxy ethanol or other non-ionic wetting agents. The amount of wetting agent can range from about 0.001 to 2.0 phr.

Defoamers may be used in the elastomeric article-forming composition. Defoamers may be chosen from naphthalene type defoamers, silicone type defoamers and other non hydrocarbon type defoamers or defoamers of refined oil of vegetable origin. The amount of defoamers can range from about 0.001 to 2.0 phr.

The elastomeric article-forming composition could also be blended with inorganic filler. Suitable inorganic fillers include calcium carbonate, carbon black or clay. Preferably, the amount of inorganic filler included in the blend would not exceed 75% either alone or in combination. It will be appreciated that the blended composition will retain the favorable properties.

Sensitisers are chemicals that can be used in compositions for producing elastomeric films to control the amount of the composition that will remain coated on the mould during dipping (film deposition). Examples of sensitisers known in the art that can be used in the composition for producing an elastomeric film include polyvinyl methyl ether, polypropylene glycol, ammonium nitrate and ammonium chloride. When used, the amount of sensitiser will be chosen based on the desired film thickness to remain on the mould during dipping, and will generally be between 0.01-5.0 phr. For thinner films, the amount will generally be between 0.01 to 2.0 phr, e.g. 0.1 to 1.0 phr. When other techniques are used for controlling the film thickness on the mould, such as the use of pre-dipping the mould into coagulant before undertaking the multiple dipping into the composition for producing the elastomeric film, the composition for producing an elastomeric film may not require a sensitiser.

Those skilled in the art will readily be able to vary the components of the elastomeric article or film-forming composition to suit the particular polymer used as well as the particular final article desired. It will also be understood by those of skill in the art that specific chemicals or compounds which have been listed above are intended to be representative of conventional materials that may be used in formulating the elastomeric film-forming composition and are merely intended as non-limiting examples of each such component of the composition.

Preparation of Elastomeric Articles, Such as Films

The latex composition having the desired composition is formed into the shape of the desired article, and then cured. Curing is used in a general sense, to refer to the stage during which cross-linking is performed. Such curing conditions are as known in the art.

Any known techniques can be used to form the desired shape of elastomeric article, including dipping processes, extrusion and otherwise.

Set out below are brief details of one suitable technique for producing an elastomeric article using a dipping process. This is described in the context of producing a thin film glove. It should be understood that variations may be made to this process as known or described in the art. The steps in the manufacture of a film may be as generally described in PCT/AU2014/000726 and PCT/AU2014/000727, which are incorporated by reference.

Optional Step (a) Dipping the Former into a Coagulant Containing Multivalent Ions in Solution The details of this step are as described in the PCT publications referred to above. In brief, a suitable former, which is based on the shape of the article to be produced (e.g. flat for a film or glove-shaped for a glove) can be dipped into a coagulant containing multivalent ions in solution. The former is dipped into a coagulant containing multivalent ions, leaving a thin coating of the charged ions on the surface of the former. The charged ions coating can assist in controlling the amount composition for forming the elastomeric film that will subsequently remain on the surface of the mould after dipping into the composition, through charge interactions. The composition of the coagulant may be as described in the two PCT publications as described above. Cationic multivalent ion-containing coagulates are typically used, such as a calcium coagulant.

Optional Step (b) Drying or Partially Drying the Coagulant-Dipped Former

If the former is dipped into a coagulant, following this step the former is dried or partially dried.

Step (i) Dipping the Former into the Elastomeric Article-Forming Composition of the Invention to Produce a Layer of Elastomeric Article-Forming Composition on the Mould The former is dipped into the composition for producing an elastomeric film, embodiments of which have been described in detail above. The duration of dipping, temperature, and former surface temperature may be as described in the PCT publications referred to above.

Step (ii) Drying or Partially Drying the Layer of Elastomeric Film-Forming Composition on the Former The conditions and details of this step may be as described in the PCT publications referred to above.

The method of manufacture described herein encompasses the preparation of single-layered or multiple-layered elastomeric films. Therefore, in some embodiments, the method may include step (v), which involves drying and curing the layered elastomeric film on the former directly after this step to prepare a single layered elastomeric film. In other embodiments, the method may include a number of repetitions of optional steps (iii) and (iv) after this step to produce a multiple-layered elastomeric film.

Step (iii) Optionally Dipping the Former Coated with the Dried or Partially Dried Layer of Elastomeric Film-Forming Composition into the Elastomeric Film-Forming Composition to Produce a Further Layer of Elastomeric Film-Forming Composition on the Former This step is optional, and is present when multi-layer articles are produced. The details of this step are as described in the PCT publications referred to above.

Step (iv) Optionally Repeating the Drying or Partial Drying Step (ii) and the Further Dipping Step (iii)

This step is optional, and is present when multi-layered articles are produced. The number of layers may be 2, 3 or more in multi-layered articles. The details of this step are as described in the PCT publications referred to above.

Step (v) Optional Additional Steps Prior to Drying and Curing

Further steps can be taken to fine-tune the manufacture of the elastomeric film or article. The details of these steps are as described in the PCT publications referred to above. In brief, the film or article can be leached to remove extractable components, there may be a coating material applied, beading/cuffing cab be performed and/or the product may be passed through a curing or vulcanizing oven to evaporate the water in the film and enable better cross linking.

Step (vi) Drying and/or Curing the Layered Elastomeric Film on the Former

The details of this step are as described in the PCT publications referred to above.

Step (vii) Additional Steps

In any suitable sequence, addition optional steps that can be performed prior to stripping of the glove from the former include cooling, chlorination, post-curing rinsing, polymer coating and additional drying steps. The cured film may also be cooled/chlorinated/neutralized—post-leached in hot water and optionally dipped in lubricant solution or any silicone/silicone free polymers to enable easy stripping and better donning.

Step (viii) Stripping

The film or article is stripped from the former at the conclusion of the formation process.

Application of the Skin Care Composition to Elastomeric Film

The plant stem cell material or bilayer membrane-encapsulated skin care composition may be applied to the elastomeric article or immobilized on the article, by any suitable technique, including a dipping process, spraying method or a tumbling method. This also applies to the application of the combination of a skin care component (e.g. the plant stem cell material) and phospholipid.

In the case of dipping processes, or dip-coating, this is typically performed while the article (such as the glove) is still on the former, prior to stripping. The step of applying the plant stem cell material or bilayer membrane-encapsulated skin care composition (by a dipping process) can be performed at any suitable time in the article (glove) manufacturing process, following formation of the elastomeric film layer(s) on the former. It is suitably performed after curing of the elastomeric film, but prior to stripping of the cured film from the former. In such cases, the coating can be applied after curing and chlorination. The coating may be applied after washing to clean the gloves, and after drying of the cleaned gloves. In another alternative, the step of applying the plant stem cell material or bilayer membrane-encapsulated skin care composition can be performed immediately following formation of the elastomeric film layer (after dipping), and prior to drying and/or curing.

In the case of spray-coating, the timing of the step is also suitably after drying and/or curing of the elastomeric film of the elastomeric article. However, it is possible for the spray coating step to be performed after formation of the film, but prior to drying and/or curing. The film in this case may be a dipped elastomeric film, or it may be an extruded elastomeric product. The plant stem cell material or bilayer membrane-encapsulated skin care composition can in that case be spray-coated onto the extruded elastomeric article.

In the case of tumbling, the article is prepared by a dip coating method, an extrusion method or otherwise, and then the articles are tumbled with the coating composition in a tumbling process. It is ensured that the skin-contacting surface of the articles are face outwardly during the tumbling process to apply the coating to the exposed surface. In the case of dipped gloves, the gloves are inverted during stripping, and tumbled in the inverted state, prior to re-inverting ready for donning by the user.

The applicant has performed test work to determine the required conditions for the application of the skin care composition so as to enable immobilisation on the surface of the elastomeric film. It has been found that the plant stem cell material (e.g. the coating composition) is to be applied at a temperature of below 60° C., preferably below 50° C., to maintain the stability of the plant stem cell material or bilayer membrane-encapsulated skin care composition. Whilst a temperature below 50° C. is the preference, it is permissible for the coating composition or the film containing the coating composition to be subjected to higher temperature conditions (e.g. up to 60° C.) for a short duration. Such a short duration of higher temperature conditions should not affect the stability of plant stem cell material or bilayer membrane-encapsulated skin care composition, such as the liposome-encapsulated plant stem cell material. The duration of higher temperature conditions (above 50° C. but preferably below 60° C.) should not be greater than 1000 seconds, preferably not greater than 500 seconds or more preferably not greater than 200 seconds. Temperatures above 60° C. can destabilize the liposome structure and degrade the bioactivity of the plant stem cells. Maintaining the temperature conditions to a temperature of not more than 50° C. during and following application of the plant stem cell material or bilayer membrane-encapsulated skin care component is a feature of preferred embodiments of the invention. In some embodiments, the temperature is not raised above 60° C. during any stage of the coating process. In some embodiments, the temperature conditions may be not more than 48° C., not more than 46° C., not more than 44° C., not more than 42° C. or not more than 40° C.

In the preceding paragraph, the temperatures refer to the temperature of the coating composition at the time when it is applied to the elastomeric film. The temperature conditions may apply to the glove surface prior to dipping into the coating composition. The temperature of any drying step for drying of the composition and water evaporation should be maintained at a temperature below 60° C. The temperature is preferably maintained within the temperature conditions expressed in the preceding paragraph. It will be understood that the temperature of any drying oven, tumbler or spray-drying air conditions should be maintained at below 60° C., or below 50° C. The drying conditions may be temporarily raised to above 50° C. (but below 60° C.) for a time period of not greater than 1000 seconds, preferably not greater than 500 seconds, preferably not more than 200 seconds, and most preferably not more than 100 seconds. In some embodiments, the temperature during drying is maintained at a temperature of 48° C. or less, 46° C. or less, 44° C. or less, 42° C. or less, or 40° C. or less.

The coating composition is suitably dried on the glove surface to yield a dry surface. In some embodiments, the coating composition is dried to yield a dry, dehydrated surface. The coating is suitably a dry dehydrated coating.

The applicant has determined that the pH of the coating composition should be between 5.0 and 8.0, preferably between 7 and 7.5. If the pH conditions are outside of this range, then there is a risk of destabilization of the bilayer membrane system (particularly in the case of liposomes). There is also a risk of deterioration of the encapsulated material, particularly in the case of plant stem cell material. It is also necessary for the pH conditions to suit the conditions used for the manufacture of elastomeric film articles, where pH is also a factor.

The applicant has also determined that skin care coating composition should be applied as a relatively dilute aqueous suspension, having a water content of at least 50%, preferably at least 90% of the coating composition, particularly for embodiments where there is a bilayer membrane system encapsulating the skin care components, such as liposomes. This allows for the liposomes to be applied intact. Prolonged shelf stability may also be aided by this factor.

Variations

In addition to or in place of the liposome delivery system, other techniques could be used to immobilise plant stem cell material on the surface of the elastomeric article.

A hydrogel containing the plant stem cell material could be prepared and coated on the elastomeric article or film. The hydrogel could contain water or may be applied and dried into a dehydrated form retaining the plant stem cell material within. A hydrogel or other coating composition could be used together with the bilayer membrane encapsulated skin care component (or plant stem cell material). A coupling agent could be used to couple the liposomes (or other encapsulating system substance) to the glove surface.

A mixed coating, or a multi-layered coating, could be used. The multilayered coating may be based on the skin care composition coating as a one of the layers, and a second (and optionally further) coating layer.

The second coating layer could be a pre-coating or a post-coating layer; pre-coating is preferred to allow for closer proximity of the plant stem cell material or skin care component to the skin of the person coming into contact with the elastomeric article. The mixed or multilayered coating system may comprise hydrogels, second coating compositions or coupling agents, or combinations thereof. In the case of a hydrogel pre-coating, such a pre-coating layer may be applied prior to application of the skin care composition coating. The immobilisation layer may comprise a hydrogel, such as polyethylene glycol, or a biosealant (a biopolymer derivative rendering adhesive properties for the immobilization of the plant stem cell material or bilayer membrane-encapsulated skin care composition). Whilst such a layer can improve the immobilization of the plant stem cell material or bilayer membrane-encapsulated skin care component on the glove surface, some plant stem cell material or bilayer membrane-encapsulated skin care component can still adhere to the glove surface without an immobilization layer.

Figure 7:
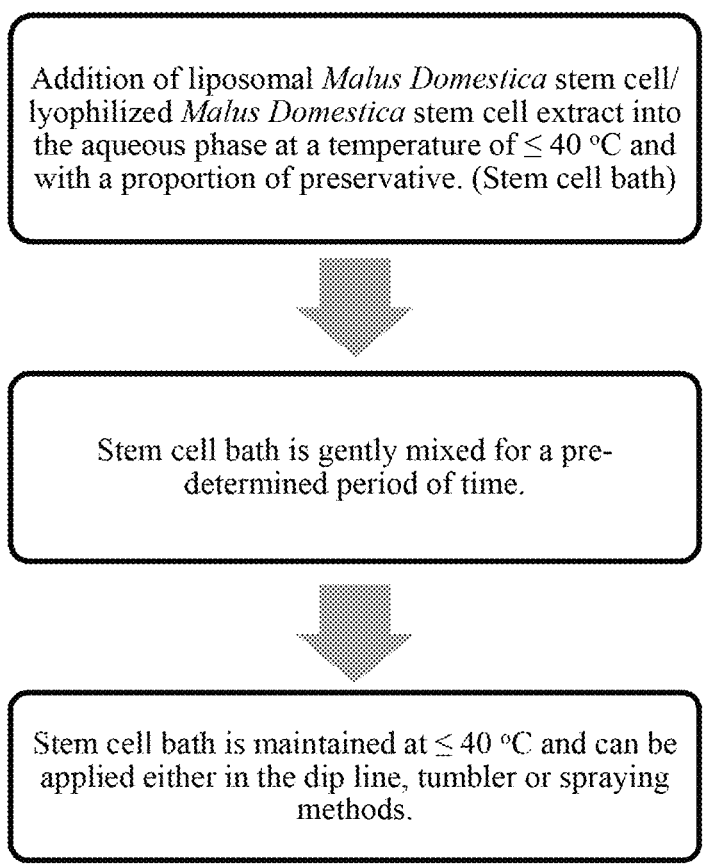
FIG. 7 is a flow diagram showing the stages in the production of a stem cell-containing coating composition in accordance with embodiments of the present application.

Preparation of the Plant Stem Cell Material or Bilayer Membrane-Encapsulated Skin Care Composition Prior to Application onto Elastomeric Film In this section the preparation of plant stem cell material is described, followed by a process for the encapsulation of the plant stem cell material in liposomes, as a form of bilayer membrane system. This is described with reference to the embodiment where the plant stem cells are *Malus Domestica* stem cells, and the liposomes are based on lecithin as the lipid. The steps in the process are represented diagrammatically in FIG. 7.

To prepare the plant stem cells, plant tissue from the selected plant species is taken, sterilised, and the tissue is subjected to conditions to promote callus formation, from which plant stem cells can be collected. These conditions typically involve placing the tissue into induction media and culturing in the presence of a suite of induction chemicals (including hormones and nutrients) that promote the generation of dedifferentiated plant stem cells. The plant stem cells are collected, and cultured in bioreactors of suitable size for the production of the required volume of plant stem cells. Culturing conditions and processes are well known in the art. Suitable culturing media may include sucrose, auxins, cytokinins, gibberellins, macronutrients and micronutrients. Such propagation in vitro is used to grow genetically identical copies of plant stem cells with desirable characteristics. The properties of the cells harvested are independent of the season.

Plant Stem Cells are Harvested and used in the Production of the Liposomes.

Liposomes containing the plant stem cell material can be prepared by combining the selected amphipathic molecule for forming the bilayer membrane (such as lecithin, as an example of a phospholipid) with plant stem cells in the presence of water, and applying energy to form liposomes of the desired size containing plant stem cell material. The process of energy application to produce the liposomes has the effect of simultaneously lysing the plant stem cells, such that the plant stem cell material incorporated into the liposomes is a plant stem cell lysate. The amphipathic molecules may be in the form of an aqueous solution when combined with an aqueous suspension of the plant stem cells. Energy is typically applied by way of high pressure homogenization. This is a useful technique to simultaneously lyse plant stem cells obtained from suspension cultures and to encapsulate the cell lysate (or at least the soluble fraction thereof) in formed liposomes. The cell lysate contains the epigenetic factors, and these are incorporated into the liposomes. Further details for the production of liposomes of plant stem cell material may be found in U.S. Pat. No. 9,155,916, the contents of which are incorporated herein by reference.

The energy application during the liposome formation step is controlled so as to produce liposomes of the desired size. In the case of small unilamellar vesicles or liposomes having a size ranging from 20 nm-100 nm in diameter, energy is applied in the form of a pressure homogenisation at about 800-1500 bar ($0.8$-$1.5 \times 10^8$ N/m$^2$). The energy applied may be around 1200 bar. For larger liposomes, the energy application may be suitably adjusted.

The liposomes so produced are suspended in an aqueous media. The liposomes are combined with any other components such as preservative and diluted as required, while maintaining a temperature of 40° C., to form a stem cell bath. The stem cell bath is gently mixed for a predetermined time period. The stem cell bath is maintained at 40° C. during mixing. The composition in stem cell bath can be used to coat the gloves either through dipping gloves into the stem cell bath in a dip line, through application to the gloves in a tumbler or through spraying methods (see description above). The steps in the production of the stem cell bath are indicated schematically in FIG. 7.

In practice, an initial stem cell composition containing a particular % content of stem cell material may be prepared, ready for dilution and use. This may be referred to as a "stock solution". The stock solution may have a concentration in the range of 1% to 20%. This stock solution may then be diluted as desired to the target concentration for the plant stem cell material for the coating composition. During dilution, other agents may be added. The stock solution may be diluted to a 0.01%-10% solution strength. This means that a 0.01% to 10% amount of the stock is taken (itself having a particular plant stem cell material concentration), and is diluted with water (to a total of 100%). Through this process, the coating composition concentration can be adjusted through dilution by adding at least 90% water (i.e. 10% or less stock solution, 90% or more water) prior to application to the elastomeric film surface. In general terms, the coating composition has a water content of at least 50% by weight at the time of application of the coating composition onto the surface of the elastomeric film. In some embodiments, the water content of the coating composition at this time is at least 90%.

To check for the presence of plant stem cells on the glove surface, the liposomal plant stem cells can be incorporated with fluorescent dye 6-carboxyfluorescein, so as to allow observation under a fluorescent microscopy system, and to provide an indication of the presence (and coverage) of liposomal particles on the glove inner surface. The morphology of the attached and adsorbed liposomal *Malus Domestica* stem cells on the elastomeric surface can also be observed under an atomic force microscopy (AFM), scanning electron microscopy (SEM) and transmission electron microscopy (TEM) systems.

It is reported that *Malus Domestica* stem cell extract stimulates colony-forming efficiency (CFE) of keratinocyte progenitor cells in culture and enhanced gene expression of senescent dermal fibroblasts as well as protective against oxidative stress, the bio-markers such as cyclin B1, cyclin E1, p53 tumor suppressor gene, insulin-like growth factor II, heme oxygenase I could be used as indicator. Extending from this work, the applicants have been able to immobilise such plant stem cell material onto the surface of gloves. Test subjects have worn glove samples for 4 hours per day for a duration of at least several weeks, and have reported improved skin moisturization, and smoother skin.

In the claims and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

EXAMPLES

The invention will now be described in further detail with reference to the following non-limiting examples which involve the preparation of elastomeric film gloves containing the skin care composition produced in accordance with embodiments of the invention.

Production of Liposomes of Plant Stem Cell Lysate

Approximately 1-3 cm diameter pieces of *Malus Domestica* apples as plant stem cell progenitor material are obtained by means of borer apparatus. The obtained progenitor material are sterilized by treatment with 70% ethanol for 30 seconds followed by treatment with 2.5% sodium hypochloride containing 0.1% Tween 40. The progenitor material is washed at least three times in distilled water and sectioned into slices of 2-4 mm thickness. The slices are deposited on solid culture medium (pH5.6, 0.8% agar) in the presence of agents for cell growth containing: calcium chloride (332 mg/L), potassium dihydrogen phosphate (170 mg/L), potassium nitrate (1900 mg/L), magnesium sulfate (180.54 mg/L), ammonium nitrate (1650 mg/L), cobalt chloride hexahydrate (0.025 mg/L), copper sulfate pentahydrate (0.025 mg/L), iron-sodium-EDTA (36.7 mg/L), boric acid (6.2 mg/L), potassium iodide (83 mg/L), manganese sulfate hydrate (16.9 mg/L), disodium molybdate dihydrate (0.25 mg/L), zinc sulfate heptahydrate (8.6 mg/L), myo-Inositol (100 mg/L), nicotinic acid (5 mg/L), glycine (2 mg/L), pyridoxine hydrochloride (0.5 mg/L), thiamidine hydrochloride (0.5 mg/L), folic acid (0.5 mg/L), biotin (0.05 mg/L), ascorbic acid (50 mg/L), thiourea (25 mg/L), L-Asparagine (180 mg/L), sucrose (3000 mg/L).

The cultures are incubated at 25° C. in the absence of light for two to three weeks until the induction of the primary callus. Formed calluses are harvested and subcultured until callus dedifferentiation is complete.

A liquid suspension culture comprising dedifferentiated cells is generated using cells obtained from the callus. Cells are homogenized and grown presence of the above defined liquid culture media without agar, and incubated at 25° C. in the absence of light, with 100 rpm shaking velocity.

The growth culture is scaled-up to a bioreactor by transferring 40-60% of cells by weight from the liquid suspension culture to the bioreactor. The culture is incubated at 25° C. in the absence of light with 100 rpm shaking velocity and aeration 0.1 vvm, for 20 days.

Dedifferentiated plant stem cells are produced by a supplier from *Malus Domestica*. The stem cells are subjected to pressure homogenisation at ~1200 bar ($1.2 \times 10^8$ N m−2) in the presence of lecithin and glycerol, amongst other components, to produce liposomes containing the *Malus Domestica* stem cell material (stem cell lysate). The final liposomal stem cell material contains 9% stem cell material (weight to volume), with the balance made up of lecithin (as the phospholipid forming liposomes of the plant stem cell material), glycerol, xanthan gum as thickener/stabiliser, phenoxyethanol as preservative and water.

The 9% liposomal stem cell material composition is further diluted to a water content of 99.5% (although it could be diluted to any concentration between 50 and 99.5% with the balance being the dry weight of the stem cell lysate-containing liposomes), to produce the dipping composition for the subsequent formation of the skin care coating on gloves.

Glove Production

Gloves were prepared from the following composition set out below using standard elastomeric film production processes as known in the art.

Examples 1 and 2

TABLE 1

| Ingredients - Example 1 | Parts per Hundred Rubber (phr) - Dry basis (unless otherwise indicated) |
|---|---|
| Elastomer - carboxylated acrylonitrile butadiene latex (Nantex 6772) | 100 |
| Cross-linking agent - zinc oxide | 1.0 |
| Accelerator - ZDBC | 0.5 |
| Sulphur | 1.2 |
| Antioxidant | 0.5 |
| Opaqueness provider | 1.5 |
| Pigment | As per requirement |
| Defoamer | 0.1 |

TABLE 2

| Test Parameter | NBR Concentration of liposomal *Malus Domestica* stem cell (%) in coating composition | | | | | | |
|---|---|---|---|---|---|---|---|
| | 0* | 0.009** | 0.0045 | 0.045 | 0.27 | 0.45 | 0.9*** |
| Tensile (MPa) | 30.83 | 30.96 | 31.33 | 33.47 | 28.74 | 30.43 | 29.31 |
| Modulus at 300 (MPa) | 4.33 | 4.70 | 5.06 | 4.74 | 4.33 | 4.92 | 4.45 |
| Modulus at 500 (MPa) | 12.06 | 13.20 | 14.65 | 13.42 | 12.52 | 13.25 | 11.43 |
| Elongation (%) | 603 | 609 | 591 | 627 | 600 | 602 | 613 |
| Force at Break (N) | 7.70 | 8.68 | 7.90 | 8.25 | 8.95 | 8.05 | 8.68 |

*Control - Dipped in plain water.
**1 part of the 9% stem cell solution was diluted by a factor of 1000 with water.
***1 part of the 9% stem cell solution was diluted by a factor of 10 with water - i.e. a 10% solution of the stock solution (which was 9% stem cell material) was used.

TABLE 3

| Ingredients - Example 2 | Parts per Hundred Rubber (phr) - Dry basis (unless otherwise indicated) |
|---|---|
| Elastomer - carboxylated acrylonitrile butadiene latex (Nantex 6772) | 100 |
| Cross-linking agent - zinc oxide | 0.1 |
| Accelerator - ZDBC | 0.25 |
| Sulphur | 0.15 |
| Antioxidant | 0.5 |
| Opaqueness provider | 2.0 |
| Pigment | As per requirement |
| Defoamer | 0.001 |

TABLE 4

| Test Parameter | NBR Concentration of liposomal *Malus Domestica* stem cell (%) in coating composition | | | | | | |
|---|---|---|---|---|---|---|---|
| | 0 | 0.009 | 0.0045 | 0.045 | 0.27 | 0.45 | 0.9 |
| Tensile (MPa) | 18.57 | 20.37 | 24.61 | 18.93 | 19.33 | 22.21 | 20.98 |

TABLE 4-continued

| Test Parameter | NBR Concentration of liposomal *Malus Domestica* stem cell (%) in coating composition | | | | | | |
|---|---|---|---|---|---|---|---|
| | 0 | 0.009 | 0.0045 | 0.045 | 0.27 | 0.45 | 0.9 |
| Modulus at 300 (MPa) | 2.09 | 2.58 | 2.40 | 2.17 | 2.36 | 2.27 | 2.22 |
| Modulus at 500 (MPa) | 3.91 | 3.87 | 4.54 | 4.34 | 4.60 | 4.81 | 4.49 |
| Elongation (%) | 740 | 740 | 750 | 700 | 720 | 710 | 710 |
| Force at Break (N) | 6.16 | 6.15 | 6.42 | 6.34 | 6.23 | 6.26 | 6.59 |

Coating composition information as for Table 2

The process used involved dipping a glove-shaped former into a coagulant composition, drying, dipping into the elastomeric film-forming composition (see compositions of Examples 1 and 2 set out in Tables 1 and 3 above) at a total solid content of 44.5% and temperature of 60-120° C. to produce a film layer on the former, drying the layer, and curing to produce a cured glove-shaped elastomeric film on the former. The gloves had an average thickness of 0.10 mm, measured in accordance with procedures known in the art.

Prior to stripping of the gloves from the former, the gloves were dipped into the liposome compositions set out in Tables 2 and 4 above for each of Examples 1 and 2, respectively. The glove surfaces prior to application of the liposome composition had a temperature of 35° C., and the liposome compositions were held at a temperature of 4≤40° C. during dipping. The pH of the liposome compositions was 7.4. The gloves were dipped into the liposome composition for a time period of 60 seconds (this can be varied between 1 and 300 seconds—counted from the time of complete immersion of the former until commencement of removal of the former from the dipping tank).

The coating composition was dried by way of progressing through a drying tunnel held at a temperature of 37° C. The gloves were then stripped from the formers.

Sample squares (3 cm×3 cm) of films produced in accordance with the method described above were prepared (based on a concentration 0.45% plant stem cell material in the coating composition), and were placed in contact with the skin on the forearm of test subjects, for a time period of 4 hours per day, over a time period of one week. The use of flat sample squares in the test was designed to avoid the influence of perspiration that can occur when wearing gloves, which can give a false sense of moisturising. The test subjects reported improved skin moisturization, reduced appearance of wrinkles/fine lines and smoother skin.

Testing of Glove Properties

Glove are tested to determine the following properties:
Modulus at 300%
Modulus at 500%
Tensile strength (MPa/Psi) (1 MPa=145 Psi); and
Elongation %.

Tensile strength, stress at 300% and 500% modulus and elongation to break are measured by testing procedures conducted in accordance with ASTM D 412-06a (2013), based on the sample size set by the standard for gloves. The gloves are also tested for force at break measured in accordance with EN 455. The standards are readily available. These tests can be applied to multilayer films and gloves (such as examination gloves for medical applications). Tensile strength, modulus at 300% and modulus at 500% are each measured in units of MPa, and the elongation (or elongation at break) in %. The results for the films produced in accordance with Examples 1 and 2 are set out in Tables 2 and 4, respectively.

Example 3

Introduction

In this example, a coating composition containing liposome-encapsulated apple stem cells (Set 1) was prepared and tested against like compositions, but for the removal of the additives (Set 2), or the removal of the encapsulated apple stem cells (Set 3). The additives serve to enhance the pick-up of apple stem cell and to aid immobilisation of the apple stem cell materials to the donning side of the glove. Several additives were studied to enhance the pick-up of the apple stem cell.

Methodology

1. A stock solution of apple stem cell encapsulated in liposome as described above was combined with additives in accordance with the formulations set out in Table 5 to prepare three sets of coating solutions. Note that Set 2 omits the three additives and Set 3 omits the apple stem cell component.

TABLE 5

| | Percentage (%) | | |
|---|---|---|---|
| Ingredient | Set 1 | Set 2 | Set 3 |
| Apple stem cell encapsulated in liposome | 1 | 1 | 0 |
| Rheology modifier[1] | 0.08 | 0 | 0.08 |
| Wetting agent[2] | 0.1 | 0 | 0.1 |
| Preservative[3] | 0.2 | 0 | 0.2 |
| Water | 98.62 | 99 | 99.62 |

[1]Any suitable rheology modifier can be used - xanthan gum was used here. Note this is additional to any minor xanthan gum component that may be present in the liposome-encapsulated apple stem cell component as described previously.
[2]Any suitable surfactant can be used - a Teric surfactant, being an alcohol ethoxylate, was used here.
[3]Any preservative can be used - phenoxyethanol was used here.

2. The weight of the glove without coating was recorded. The glove compostion was that set out in Table 3/Example 2 above.
3. The gloves were inverted and put onto ceramic former. Donning side of the glove was facing outward.
4. The former with glove was heated in the oven at a temperature of 50 to 60° C. before being dipped into the coating solution.
5. The coating was dried in oven at a temperature of 50 to 60° C. for 5 minutes. Thereafter the glove was stripped from the former.

6. Weight of the glove with coating was determined. Weight difference before and after coating was measured.
7. Control glove without any coating (set in Table 5) was also prepared.

Result and Discussion
1. Table 6 below shows the weight difference before and after the glove coating with coating solution.

TABLE 6

| Sample | Weight of glove without coating (g) | Weight of coated glove (g) | Weight of coating (g) | Average |
|---|---|---|---|---|
| Set 1 (Apple stem Cell with additives) | | | | |
| Replicate 1 | 3.247 | 3.266 | 0.019 | 0.018 |
| Replicate 2 | 3.411 | 3.429 | 0.018 | |
| Replicate 3 | 3.5 | 3.517 | 0.017 | |
| Set 2 (Apple stem cell without additives) | | | | |
| Replicate 1 | 3.466 | 3.47 | 0.004 | 0.004 |
| Replicate 2 | 3.45 | 3.454 | 0.004 | |
| Replicate 3 | 3.26 | 3.264 | 0.004 | |
| Set 3 (Additives without apple stem cell) | | | | |
| Replicate 1 | 3.258 | 3.269 | 0.011 | 0.0097 |
| Replicate 2 | 3.486 | 3.494 | 0.008 | |
| Replicate 3 | 3.461 | 3.471 | 0.01 | |
| Control (Without coating) | | | | |
| Replicate 1 | 3.375 | 3.375 | 0 | 0 |
| Replicate 2 | 3.554 | 3.554 | 0 | |
| Replicate 3 | 3.293 | 3.293 | 0 | |

2. Apple stem cell without additives (in particular the rheology modifier) has poor pick up. The weight of apple stem cell on donning side is only 0.004 g.
3. Weight of apple stem cell coated on the donning side increased 107.5% from 0.004 to 0.0083 g (Set 1-Set 3) after the apple stem cell was mixed with additives. This is indicated by the weight difference of coating in Set 1 and coating in Set 3.
4. Additives assist in ensuring even distribution of apple stem cell on the donning surface and to improve pick-up of apple stem cell.

Example 4

Figure 8:
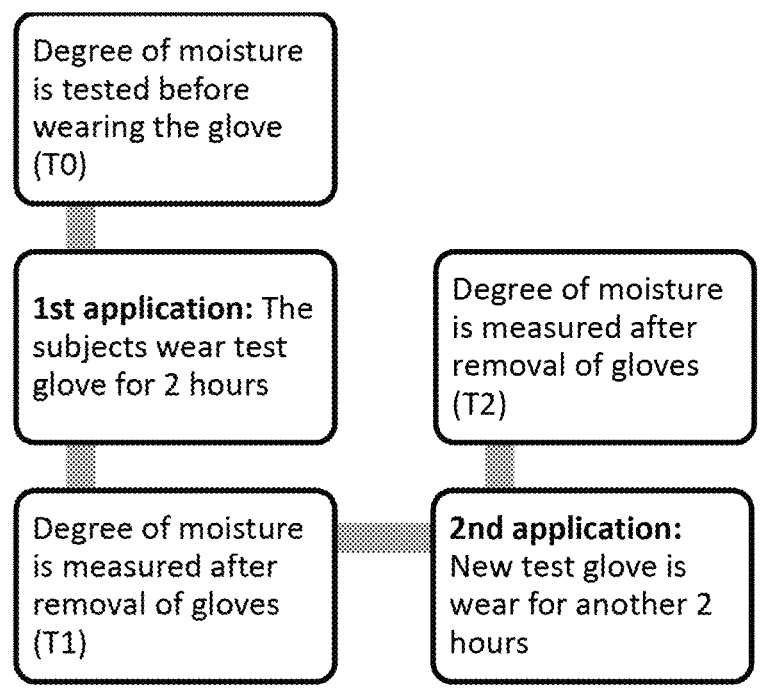
FIG. 8 is a flow diagram showing the stages in testing the moisturising effect of gloves in accordance with an embodiments of the invention.

Assessment of Immediate Moisturising Effect Before and After Wearing of Apple Stem Cell Coated NBR Glove Study Subject:
Number of subject: 20 human subjects
Age: 24 to 50 years old Procedure:
1. Prior to conducting the measurement for moisturising effect, the subjects were conditioned for 30 minutes in an air conditioned room (20±2° C., 40-60±5% relative humidity) with their hands uncovered to let the skin adapt to the temperature and humidity of the room.
2. About 1 cm$^2$ of the right dorsal surface of the hand was identified as the test area. Each subject was instructed not to use any product on the test area 3 days prior to and throughout the study.
3. Moisturising effect was indicated by degree of skin moisturise and it was measured using a Corneometer Model MPA 2 (Brand: Courage & Khazaka Cologne, Germany).
4. After the basal measurements were recorded (T0), the subjects were instructed to wear the test glove based on the glove fomulation of Table 7 (same as Table 3/Example 2) with the coating formulation of Table 8 to cover test area for 2 hours. Then, the test glove was removed and the degree of moisture was recorded as T1.
5. The subject then wore a new set of test glove for another 2 hours. The changes in the degree of moisture was then recorded as T2.
6. The procedure for assessing the moisturising effect is shown in FIG. 8.

TABLE 7

| Ingredients - Example 2 | Parts per Hundred Rubber (phr) - Dry basis (unless otherwise indicated) |
|---|---|
| Elastomer - carboxylated acrylonitrile butadiene latex (Nantex 6772) | 100 |
| Cross-linking agent - zinc oxide | 0.1 |
| Accelerator - ZDBC | 0.25 |
| Sulphur | 0.15 |
| Antioxidant | 0.5 |
| Opaqueness provider | 2.0 |
| Pigment | As per requirement |
| Defoamer | 0.001 |

TABLE 8

| Ingredient | Percentage (%) |
|---|---|
| Apple Stem Cell encapsulated in liposome | 2 |
| Rheology modifier | 0.1 |
| Wetting agent | 0.1 |
| Preservative | 0.2 |
| Water | 97.6 |

Statistical Analysis:
1. A paired T-test was used to analyse the degree of changes following treatment.
2. The mean difference in the degree of skin moisture for the area treated with test glove was compared to their baseline using paired samples T-test.
3. The differences between the two groups of data were considered significant if the probability p was ≤0.05.

TABLE 9

| No. | Baseline (T0) | 2 hours (T1) | 4 hours (T2) | T1-T0 | T2-T0 |
|---|---|---|---|---|---|
| Mean | 29.80 | 31.97 | 33.78 | 2.17 | 3.98 |
| Standard Deviation | 4.08 | 3.94 | 4.58 | 1.99 | 3.08 |
| Paired T-test (p-value) | | 0.00* | 0.00* | 0.00* | 0.00* |

*Significant difference

Result:
The degree of skin moisture on the treated area with test glove was improved significantly after 2 hours of application. The mean difference was 2.17±1.99 (p=0.00). The improvement remains significant even after 4 hours of glove application. The mean difference was 3.98±3.08 (p=0.00).

Overall, the nitrile glove coated with apple stem cell has significant short-term moisturising effect.

Example 5

Test for Irritation and Skin Sensitisation (ISO 10933-10:2010)

Introduction:

This study was conducted to assess the potential of nitrile glove coated with Apple Stem Cell to produce dermal irritation following exposure to the skin of rabbits. A skin sensitisation test is conducted to assess the potential of nitrile glove coated with Apple Stem Cell to cause a delayed hypersensitivity (Type IV) immunological response through contact with the skin of guinea pigs. The reaction is primarily due to substances that leach out of the test glove. Both irritation and skin sensitisation tests are conducted according to standard method described in ISO 10993-10:2010, Biological evaluation of medical devices—Part 10: Tests for irritation and skin sensitization.

Methodology:

Test for Irritation

1. A sample glove was placed with each of the inner and outer surface in direct contact with the intact skin of each rabbit under a patch of double layer surgical gauze. The sample glove had a glove formulation of Table 12 (same as Table 3/Example 2) and a coating formulation of Table 13.
2. Two additional sites which were identified for positive control, sodium dodecyl sulfate (SDS) in petroleum jelly and negative control (normal saline) was respectively held in contact with the skin using a patch of double layered gauze.
3. The patches were occluded with occlusive material for 24 hours and maintained with the help of bandages.
4. Cutaneous macroscopical examinations were performed at 1±0.1, 24±2, 48±2 and 72±2 hours after removal of test glove.
5. Skin reaction was evaluated based on the scoring system shown in Table 10.

TABLE 10

| Reactions | Description | Score |
| --- | --- | --- |
| Erythema (E) | No erythema | 0 |
| | Very slight erythema (barely perceptible) | 1 |
| | Well-defined erythema | 2 |
| | Moderate erythema | 3 |
| | Severe erythema (beet redness) to eschar formation preventing grading of erythema | 4 |
| Oedema (O) | No oedema | 0 |
| | Very slight oedema (barely perceptible) | 1 |
| | Well-defined (edges of area well-defined by definite raising) | 2 |

TABLE 10-continued

| Reactions | Description | Score |
| --- | --- | --- |
| | Moderate oedema (raised approximately 1 mm) | 3 |
| | Severe oedema (raised more than 1 mm and extending beyond exposure area) | 4 |
| | Maximal possible score for irritation | 8 |

Test for Skin sensitisation

1. The test glove was topically applied onto the left side of eleven healthy guinea pigs for 6±0.5 hours, three times a week for a three weeks induction period.
2. Fourteen days after the last induction, a challenge dose was applied onto a naive site on the right side of each guinea pig for 6±0.5 hours.
3. The skin was examined for allergic reactions and the intensity of reaction is examined at 0±2, 24±2 and 48±2 hours after removal of patch in the challenge phase.
4. Skin sensitisation respond was assessed according to the Magnusson and Kligman scale described in Table 11.

TABLE 11

| Patch test reaction | Grading scale |
| --- | --- |
| No visible change | 0 |
| Discrete or patchy erythema | 1 |
| Moderate and confluent erythema | 2 |
| Intense erythema and swelling | 3 |

Result:

Test for Irritation

1. There was no erythema or oedema noted on the test site after 1±0.1, 24±2, 48±2 and 72±2 hours. The Primary Irritation Index (PII) is 0.
2. Cutaneous changes at the site of contact with positive control (SDS in petroleum jelly) is observed with evidence of erythema and oedema noted on most test sites after 1±0.1, 24±2, 48±2 and 72±2 hours. The Primary Irritation Index (PII) is 8.
3. Nitrile glove coated with apple stem cell is not corrosive and the primary irritation response is therefore negligible.

Test for Skin Sensitisation

1. No reaction was observed upon removal of the test glove during the induction and challenge phase.
2. No reaction was observed in the negative control animals.
3. All out of eleven guinea pigs in the positive control group were sensitised with grading scale of 1 to 2. 1-Chloro-2,4-Di-Nitrobenzane (DNCB) was used as positive control material.
4. Nitrile glove coated with apple stem cell does not induce skin sensitisation on the guinea pigs.

TABLE 12

| Ingredients - Example 2 | Parts per Hundred Rubber (phr) - Dry basis (unless otherwise indicated) |
| --- | --- |
| Elastomer - carboxylated acrylonitrile butadiene latex (Nantex 6772) | 100 |
| Cross-linking agent - zinc oxide | 0.1 |
| Accelerator - ZDBC | 0.25 |
| Sulphur | 0.15 |
| Antioxidant | 0.5 |
| Opaqueness provider | 2.0 |
| Pigment | As per requirement |
| Defoamer | 0.001 |

TABLE 13

| Ingredient | Percentage (%) |
|---|---|
| Apple Stem Cell encapsulated in liposome | 2 |
| Rheology modifier | 0.1 |
| Wetting agent | 0.1 |
| Preservative | 0.2 |
| Water | 96.1 |

Example 6

Physical properties of Glove Before and After Stem Cell Coatings Introduction

Testing of glove properties was conducted to examine whether there was a change in the glove properties after the coating process. Two different glove types were tested—nitrile gloves (formulation of Table 14) and polychloroprene gloves (formulation of Table 15). The test procedure followed was the same as for Examples 1 and 2 described previously.

Latex Formulation:

TABLE 14

| Nitrile Glove | |
|---|---|
| Ingredients | Parts per Hundred Rubber (phr) - Dry basis (unless otherwise indicated) |
| Elastomer - carboxylated acrylonitrile butadiene latex (Nantex 6772) | 100 |
| Cross-linking agent - zinc oxide | 0.1 |
| Accelerator - ZDBC | 0.25 |
| Sulphur | 0.15 |
| Antioxidant | 0.5 |
| Opaqueness provider | 2.0 |
| Pigment | As per requirement |
| Defoamer | 0.001 |

TABLE 15

| Polychloroprene glove | |
|---|---|
| Ingredients | Parts per Hundred Rubber (phr) - Dry basis (unless otherwise indicated) |
| Elastomer - Polychloroprene | 100 |
| Cross-linking agent - zinc oxide | 5.0 |
| pH stabiliser | 0.3 |
| Accelerator - ZDBC | 1 |
| Sulphur | 1 |
| Antioxidant | 1 |
| Opaqueness provider | 1.0 |
| Pigment | As per requirement |
| Defoamer | 0.005 |

Composition of Apple Stem Cell Coating:

TABLE 16

| | Percentage (%) | | |
|---|---|---|---|
| Ingredient | A | B | C |
| Apple Stem Cell encapsulated in liposome | 2 | 1 | 1 |
| Alpine Rose stem cell encapsulated in liposome | 0 | 1 | 0 |

TABLE 16-continued

| | Percentage (%) | | |
|---|---|---|---|
| Ingredient | A | B | C |
| Argan stem cell encapsulated in liposome | 0 | 0 | 1 |
| Rheology modifier | 0.1 | 0.1 | 0.1 |
| Wetting agent | 0.1 | 0.1 | 0.1 |
| Preservative | 0.2 | 0.2 | 0.2 |
| Water | 96.1 | 96.1 | 96.1 |

Result and Discussion:

TABLE 17

| | Nitrile Glove | | | | Chloroprene Glove | |
|---|---|---|---|---|---|---|
| Test Parameter | Without coating | Coating A | Coating B | Coating C | Without coating | Coating A |
| Tensile (MPa) | 18.57 | 19.14 | 20.98 | 17.20 | 19.34 | 19.62 |
| Modulus at 300 (MPa) | 2.09 | 1.80 | 2.05 | 2.00 | 1.82 | 1.79 |
| Modulus at 500 (MPa) | 3.91 | 3.55 | 3.56 | 3.61 | 3.78 | 3.86 |
| Elongation (%) | 740 | 780 | 800 | 760 | 760 | 780 |
| Force at Break (N) | 6.16 | 6.46 | 6.09 | 6.00 | 5.38 | 5.37 |

1. The plant stem cell coating did not affect the glove properties significantly. The plant stem cell material extracted from different plants did not change glove properties significantly.
2. The same outcome was observed for polychloroprene gloves.

Items Describing the Invention:

1. An elastomeric article comprising an elastomeric film and a plant stem cell material on a surface thereof.
2. The elastomeric article of item 1, wherein the plant stem cell material is a dedifferentiated plant stem cell material.
3. The elastomeric article of item 1 or item 2, wherein the plant stem cell material is in the form of the whole stem cell material.
4. The elastomeric article of any one of the preceding items, wherein the plant from which the plant stem cell material is derived is from the subkingdom Plantae and Kingdom Archaeplastida.
5. The elastomeric article of item 4, wherein the plant is selected from: plants of the Rosaceae family, apple varieties, grape varieties, Symphytum, alpine rose, argan trees, dwarf soapwort, tea plants under Family Theaceae, *Aloe Vera* under Family Asphodelaceae, *Citrus* under Family Rutaceae, *Cucumis* under Family Cucurbitaceae, Hibiscus under Family Malvaceae, *Lavandula* under Family Lamiaceae, *Calendula* under Family Asteraceae, Witch Hazel, Neem trees, Avocado trees and Algae.
6. The elastomeric article of item 4, wherein the plant from which the plant stem cell material is derived is of the Rosaceae family.
7. The elastomeric article of item 4, wherein the plant is *Malus Domestica*.
8. The elastomeric article of any one of the preceding items, wherein the plant stem cell material is in the form of plant stem cell lysate.
9. The elastomeric article of any one of the preceding items, wherein the plant stem cell material is an encapsulated plant stem cell material, in which the plant stem cell material is encapsulated in a bilayer encapsulating system or a non-bilayer encapsulating system.

10. The elastomeric article of item 9, wherein the encapsulated plant stem cell material is immobilised on a surface of the article.

11. The elastomeric article of item 9 or item 10, wherein the encapsulated plant stem cell material is a bilayer membrane-encapsulated plant stem cell material.

12. The elastomeric article of item 11, wherein the bilayer membrane system is selected from the group consisting of liposomes, cerasomes, ethosomes, niosomes, transfersomes, cetosome, aquasome, colloidosome, sphingosome, cubosome and the like.

13. The elastomeric article of item 11, wherein the bilayer membrane system is liposomes.

14. The elasotmeric article of item 13, wherein the liposomes of plant stem cell material comprise a phospholipid and plant stem cell material.

15. The elastomeric article of any one of items 13 and 14, wherein the liposomes are unilamellar or multilamellar.

16. The elastomeric article of any one of items 13 to 15, wherein the liposomes have an average diameter in the range of 1-1000 nm.

17. The elastomeric article of item 16, wherein the liposomes have an average diameter in the range of 20-400 nm.

18. The elastomeric article of any one of items 13 to 16, wherein the amount of bilayer membrane-encapsulated plant stem cell material is between 0.0001 and 80% by weight of the article.

19. The elastomeric article of any one of items 13 to 16, wherein the amount of bilayer membrane-encapsulated plant stem cell material is between 0.0001 and 50% by weight of the article.

19a. The elastomeric article of any one of the preceding items, wherein the plant stem cell material is in combination with a phospholipid in a coating layer on the surface of the article.

19b. The elastomeric article of any one of the preceding items, comprising two or more plant stem cell materials.

20. The elastomeric article of any one of the preceding items, wherein the amount of plant stem cell material on the surface of the article is between 0.0001 and 80% by weight of the article.

21. The elastomeric article of item 20, wherein the amount of plant stem cell material on the surface of the article is between 0.0001 and 50% by weight of the article.

22. The elastomeric article of any one of the preceding items, wherein the plant stem cell material forms or is a component of a coating layer on the elastomeric film of the article, and the coating composition constitutes between 0.0001%-80%, by weight of the total weight of the article.

23. The elastomeric article of item 22, wherein the coating composition constitutes between 0.0001 and 50% by weight of the article.

24. The elastomeric article of any one of the preceding items, in the form of a glove, condom or covering intended for contact with skin.

25. The elastomeric article of any one of the preceding items, wherein the elastomeric film has an average thickness of between 0.01 and 3.0 mm.

26. The elastomeric article of any one of the preceding items, wherein the elastomer of the elastomeric film is selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

27. An elastomeric article comprising an elastomeric film and a bilayer membrane-encapsulated skin care component.

28. The elastomeric article of item 27, wherein the skin care component is selected from the group consisting of plant stem cell material, essential oils, proteins, acids, moisturizing materials, skin care agents, skin softening agents, skin renewal agents, fats, sun filters, antioxidants, immunity stimulation agents, vitamins, lanolin, plant or botanical extracts, nuts, algae, proteins, peptides, hormones, antibodies, growth factors, genetic materials, bird nest extract, pharmaceutical agents, and combinations thereof.

29. The elastomeric article of item 28, wherein the skin care component is selected from plant stem cell material and plant or botanical extracts.

30. The elastomeric article of item 29, wherein the skin care component is a plant stem cell material.

31. The elastomeric article of item 30, wherein the plant stem cell material is a dedifferentiated plant stem cell material.

32. The elastomeric article of item 30 or item 31, wherein the plant stem cell material is in the form of the whole stem cell material.

33. The elastomeric article of any one of items 30 to 32, wherein the plant is *Malus Domestica*.

34. The elastomeric article of any one of items 30 to 33, wherein the plant stem cell material is in the form of plant stem cell lysate.

35. The elastomeric article of any one of items 27 to 34, wherein the skin care component constitutes between 0.0001 and 80% by weight of the total weight of the bilayer membrane-encapsulated skin care component.

36. The elastomeric article of any one of items 27 to 35, wherein the bilayer membrane system is selected from the group consisting of liposomes, cerasomes, ethosomes, niosomes, transfersomes, cetosome, aquasome, colloidosome, sphingosome, cubosome and the like.

37. The elastomeric article of item 36, wherein the bilayer membrane system is liposomes.

38. The elastomeric article of item 37, wherein the liposomes of the skin care component comprise a phospholipid and the skin care component.

39. The elastomeric article of any one of items 37 to 38, wherein the liposomes have an average diameter in the range of 1-1000 nm.

40. The elastomeric article of item 39, wherein the liposomes have an average diameter in the range of 20-400 nm.

41. The elastomeric article of any one of items 27 to 40, wherein the amount of bilayer membrane-encapsulated skin care component is between 0.0001 and 80% by weight of the article.

42. The elastomeric article of any one of items 27 to 40, wherein the amount of bilayer membrane-encapsulated skin care component is between 0.0001 and 50% by weight of the article.

43. The elastomeric article of any one of items 27 to 42, wherein the bilayer membrane-encapsulated skin care component constitutes or is a component of a coating layer on the elastomeric film of the article, and the coating layer constitutes between 0.0001%-80%, by weight of the total weight of the article.

44. The elastomeric article of item 43, wherein the coating layer constitutes between 0.0001 and 50% by weight of the article.

45. The elastomeric article of any one of items 27 to 44, in the form of a glove, condom or covering intended for contact with skin.

46. The elastomeric article of any one of items 27 to 45, wherein the elastomeric film has an average thickness of between 0.01 and 3.0 mm.

47. The elastomeric article of any one of items 27 to 46, wherein the elastomer of the elastomeric film is selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

48. A method for the manufacture of an elastomeric article comprising an elastomeric film having skin care properties, the method comprising applying a plant stem cell material onto a surface of the elastomeric film.

49. The method of item 48, wherein the plant stem cell material is applied through a dipping process, spraying method or a tumbling method.

50. The method of item 49, wherein the application is through dipping, and is performed while the elastomeric film is on a former, prior to stripping.

51. The method of item 50, wherein the dipping process to apply the plant stem cell material onto the surface of the elastomeric film is performed after drying and/or curing of the elastomeric film, but prior to stripping of the dried and/or cured film from the former.

52. The method of any one of items 48 to 51, wherein the plant stem cell material is applied at a temperature of below 40° C.

53. The method of any one of items 48 to 52, wherein the plant stem cell material constitutes or forms a component of a coating composition, and the coating composition has a pH of between 5.0 and 8.0.

54. The method of any one of items 48 to 52, wherein the plant stem cell material forms a component of a coating composition, and wherein the coating composition has a water content of at least 50% by weight at the time of application of the coating composition onto the surface of the elastomeric film.

55. The method of item 54, wherein the coating composition has a water content of at least 90% by weight of the coating composition, 55a. The method of any one of items 54 and 55, wherein the coating composition is dried at a temperature below 60° C. to yield a dry surface.

56. The method of any one of items 48 to 55, wherein the plant stem cell material is a dedifferentiated plant stem cell material.

57. The method of any one of items 48 to 56, wherein the plant is *Malus Domestica*.

58. The method of any one of items 48 to 57, wherein the plant stem cell material is in the form of plant stem cell lysate.

59. The method of any one of items 48 to 57, wherein prior to application of the plant stem cell material to the elastomeric film, the plant stem cell material is encapsulated in a bilayer membrane system or a non-bilayer encapsulating system.

60. The method of item 59, wherein plant stem cell material is encapsulated in a bilayer membrane system.

61. The method of 60, wherein the bilayer membrane system is selected from the group consisting of liposomes, cerasomes, ethosomes, niosomes, transfersomes, cetosome, aquasome, colloidosome, sphingosome, cubosome and the like.

62. The method of item 61, wherein the bilayer membrane system is liposomes, and the encapsulation comprises forming liposomes from the plant stem cell material and a phospholipid.

63. The method of item 62, wherein liposomes are formed with an average diameter in the range of 1-1000 nm.

64. The method of item 63, wherein the liposomes have an average diameter in the range of 20-400 nm.

65. The method of any one of items 60 to 64, wherein the bilayer membrane-encapsulated plant stem cell material is applied in an amount of between 0.0001 and 80% by weight of the article.

66. The method of any one of items 60 to 64, wherein the bilayer membrane-encapsulated plant stem cell material is applied in an amount of between 0.0001 and 50% by weight of the article.

66a. The method of any one of items 60 to 66, wherein the plant stem cell material forms a component of a coating composition, and the coating composition comprises phospholipid.

66b. The method of any one of items 60 to 66a, the method comprising two or more plant stem cell materials onto the surface of the elastomeric film.

67. The method of any one of items 48 to 66a, wherein the plant stem cell material is applied to the surface of the article in an amount of between 0.0001 and 80% by weight of the article.

68. The method of item 67, wherein plant stem cell material is applied in an amount of between 0.0001 and 50% by weight of the article.

69. The method of any one of items 48 to 68, wherein the plant stem cell material forms or is a component of a coating layer on the elastomeric film of the article, and the coating composition is applied in an amount of between 0.0001%-80%, by weight of the total weight of the article.

70. The method of item 69, wherein the coating composition is applied in an amount of between 0.0001 and 50% by weight of the article.

71. The method of any one of items 48 to 70, wherein the article is in the form of a glove, condom or covering intended for contact with skin.

72. The method of any one of items 48 to 71, comprising forming the elastomeric film so as to have an average thickness of between 0.01 and 3.0 mm.

73. The method of any one of items 48 to 72, comprising forming the elastomeric film from an elastomeric film composition selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

74. A method for the manufacture of an elastomeric article comprising an elastomeric film having skin care properties, the method comprising immobilising a skin care component that is encapsulated by a bilayer membrane on a surface of the elastomeric film.

75. The method of item 74, wherein the bilayer membrane-encapsulated skin care component is immobilised through application of the bilayer membrane-encapsulated skin care component in a dipping process, spraying method or a tumbling method.

76. The method of item 75, wherein the immobilising is through dipping, and is performed while the elastomeric film is on a former, prior to stripping.

77. The method of item 76, wherein the dipping process to apply the bilayer membrane-encapsulated skin care component onto the surface of the elastomeric film is performed after drying and/or curing of the elastomeric film, but prior to stripping of the dried and/or cured film from the former.

78. The method of any one of items 74 to 77, wherein the bilayer membrane-encapsulated skin care component is applied at a temperature of below 40° C.

79. The method of any one of items 74 to 78, wherein the bilayer membrane-encapsulated skin care component constitutes or forms a component of a coating composition, and the coating composition has a pH of between 5.0 and 8.0.

80. The method of any one of items 74 to 79, wherein the bilayer membrane-encapsulated skin care component forms a component of a coating composition, and wherein the coating composition has a water content of at least 50% by weight at the time of application of the coating composition onto the surface of the elastomeric film.

81. The method of item 80, wherein the coating composition has a water content of at least 90% by weight of the coating composition, 82. The method of any one of items 74 to 81, wherein the skin care component is selected from the group consisting of plant stem cell material, essential oils, proteins, acids, moisturizing materials, skin care agents, skin softening agents, skin renewal agents, fats, sun filters, antioxidants, immunity stimulation agents, vitamins, lanolin, plant or botanical extracts, nuts, algae, proteins, peptides, hormones, antibodies, growth factors, genetic materials, bird nest extract, pharmaceutical agents, and combinations thereof.

83. The method of item 82, wherein the skin care component is a plant stem cell material.

84. The method of item 83, wherein the plant stem cell material is a dedifferentiated plant stem cell material.

85. The method of item 83 or item 84, wherein the plant is is *Malus Domestica*.

86. The method of any one of items 83 to 85, wherein the plant stem cell material is in the form of plant stem cell lysate.

87. The method of any one of items 74 to 86, wherein the bilayer membrane system is selected from the group consisting of liposomes, cerasomes, ethosomes, niosomes, transfersomes, cetosome, aquasome, colloidosome, sphingosome, cubosome and the like.

88. The method of item 87, wherein the bilayer membrane system is liposomes, and the encapsulation comprises forming liposomes from the skin care component and a phospholipid.

89. The method of item 88, wherein liposomes are formed with an average diameter in the range of 1-1000 nm.

90. The method of item 89, wherein the liposomes have an average diameter in the range of 20-400 nm.

91. The method of any one of items 74 to 90, wherein the bilayer membrane-encapsulated skin care component is applied in an amount of between 0.0001 and 80% by weight of the article.

92. The method of any one of items 74 to 90, wherein the bilayer membrane-encapsulated skin care component is applied in an amount of between 0.0001 and 50% by weight of the article.

93. The method of any one of items 74 to 92, wherein the bilayer membrane-encapsulated skin care component forms or is a component of a coating layer on the elastomeric film of the article, and the coating composition is applied in an amount of between 0.0001%-80%, by weight of the total weight of the article.

94. The method of item 93, wherein the coating composition is applied in an amount of between 0.0001 and 50% by weight of the article.

95. The method of any one of items 74 to 94, wherein the article is in the form of a glove, condom or covering intended for contact with skin.

96. The method of any one of items 74 to 95, comprising forming the elastomeric film so as to have an average thickness of between 0.01 and 3.0 mm.

97. The method of any one of items 74 to 96, comprising forming the elastomeric film from an elastomeric film composition selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

98. An elastomeric article comprising an elastomeric film, a skin care component, and a phospholipid for immobilisation of the skin care component on a surface of the elastomeric film.

99. The elastomeric article of item 98, wherein the skin care component is selected from the group consisting of plant stem cell material, essential oils, proteins, acids, moisturizing materials, skin care agents, skin softening agents, skin renewal agents, fats, sun filters, antioxidants, immunity stimulation agents, vitamins, lanolin, plant or botanical extracts, nuts, algae, proteins, peptides, hormones, antibodies, growth factors, genetic materials, bird nest extract, pharmaceutical agents, and combinations thereof.

100. The elastomeric article of item 99, wherein the skin care component is selected from plant stem cell material and plant or botanical extracts.

101. The elastomeric article of item 100, wherein the skin care component is a plant stem cell material.

101a. The elastomeric article of item 101, wherein the skin care component comprises two or more plant stem cell materials.

102. The elastomeric article of item 101, wherein the plant stem cell material is a dedifferentiated plant stem cell material.

103. The elastomeric article of item 101 or item 102, wherein the plant stem cell material is in the form of the whole stem cell material.

104. The elastomeric article of any one of items 101 to 103, wherein the plant is is *Malus Domestica*.

105. The elastomeric article of any one of items 101 to 104, wherein the plant stem cell material is in the form of plant stem cell lysate.

106. The elastomeric article of any one of items 98 to 105, wherein the skin care component constitutes between 0.0001 and 80% by weight of the total weight of the combination of skin care component and phospholipid.

107. The elastomeric article of any one of items 98 to 106, wherein the skin care component and phospholipid are in the form of liposomes.

108. The elastomeric article of item 107, wherein the liposomes have an average diameter in the range of 1-1000 nm.

109. The elastomeric article of item 108, wherein the liposomes have an average diameter in the range of 20-400 nm.

110. The elastomeric article of any one of items 98 to 109, wherein the total amount of the combination of skin care component and phospholipid is between 0.0001 and 80% by weight of the article.

111. The elastomeric article of any one of items 98 to 109, wherein the total amount of the combination of skin care component and phospholipid is between 0.0001 and 50% by weight of the article.

112. The elastomeric article of any one of items 98 to 111, wherein the skin care component and phospholipid are components of a coating layer on the elastomeric film of the article, and the coating layer constitutes between 0.0001%-80%, by weight of the total weight of the article.

113. The elastomeric article of item 112, wherein the coating layer constitutes between 0.0001 and 50% by weight of the article.

114. The elastomeric article of any one of items 98 to 113, in the form of a glove, condom or covering intended for contact with skin.

115. The elastomeric article of any one of items 98 to 114, wherein the elastomeric film has an average thickness of between 0.01 and 3.0 mm.

116. The elastomeric article of any one of items 98 to 115, wherein the elastomer of the elastomeric film is selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

117. A method for the manufacture of an elastomeric article comprising an elastomeric film having skin care properties, the method comprising applying a coating composition comprising a skin care component and a phospholipid onto a surface of the elastomeric film 118. The method of item 117, wherein the coating composition is applied through a dipping process, spraying method or a tumbling method.

119. The method of item 118, wherein the application is through dipping, and is performed while the elastomeric film is on a former, prior to stripping.

120. The method of item 119, wherein the dipping process to apply coating composition onto the surface of the elastomeric film is performed after drying and/or curing of the elastomeric film, but prior to stripping of the dried and/or cured film from the former.

121. The method of any one of items 117 to 120, wherein the coating composition is applied at a temperature of below 40° C.

122. The method of any one of items 117 to 121, wherein the coating composition has a pH of between 5.0 and 8.0.

123. The method of any one of items 117 to 122, wherein the coating composition has a water content of at least 50% by weight at the time of application of the coating composition onto the surface of the elastomeric film.

124. The method of item 123, wherein the coating composition has a water content of at least 90% by weight of the coating composition, 125. The method of any one of items 117 to 124, wherein the skin care component is selected from the group consisting of plant stem cell material, essential oils, proteins, acids, moisturizing materials, skin care agents, skin softening agents, skin renewal agents, fats, sun filters, antioxidants, immunity stimulation agents, vitamins, lanolin, plant or botanical extracts, nuts, algae, proteins, peptides, hormones, antibodies, growth factors, genetic materials, bird nest extract, pharmaceutical agents, and combinations thereof.

126. The method of item 125, wherein the skin care component is a plant stem cell material.

127. The method of item 126, wherein the plant stem cell material is a dedifferentiated plant stem cell material.

128. The method of item 126 or item 127, wherein the plant is is *Malus Domestica.*

129. The method of any one of items 126 to 128, wherein the plant stem cell material is in the form of plant stem cell lysate.

130. The method of any one of items 117 to 129, wherein the skin care component and phospholipid are in the form of liposomes.

131. The method of item 130, wherein liposomes are formed with an average diameter in the range of 1-1000 nm.

132. The method of item 131, wherein the liposomes have an average diameter in the range of 20-400 nm.

133. The method of any one of items 117 to 132, wherein the combination of skin care component and phospholipid is applied in a total amount of between 0.0001 and 80% by weight of the elastomeric article.

134. The method of any one of items 117 to 132, wherein the combination of skin care component and phospholipid is applied in a total amount of between 0.0001 and 50% by weight of the elastomeric article.

135. The method of any one of items 117 to 134, wherein the article is in the form of a glove, condom or covering intended for contact with skin.

136. The method of any one of items 117 to 135, comprising forming the elastomeric film so as to have an average thickness of between 0.01 and 3.0 mm.

137. The method of any one of items 117 to 135, comprising forming the elastomeric film from an elastomeric film composition selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

138. An elastomeric article comprising an elastomeric film and bilayer membrane-encapsulated plant stem cell material.

139. A method for the manufacture of an elastomeric article comprising an elastomeric film having skin care properties, the method comprising immobilising plant stem cell material that is encapsulated by a bilayer membrane on a surface of the elastomeric film.

140. An elastomeric article comprising an elastomeric film, plant stem cell material, and a phospholipid for immobilisation of the plant stem cell material on a surface of the elastomeric film.

141. A method for the manufacture of an elastomeric article comprising an elastomeric film having skin care properties, the method comprising applying a coating composition comprising plant stem cell material and a phospholipid onto a surface of the elastomeric film.

142. The method of item 141, wherein the coating comprises two or more plant stem cell materials.

The invention claimed is:

1. An elastomeric glove comprising: (a) an elastomeric film and (b) a dry coating layer on a surface thereof, wherein the dry coating layer contains an effective amount of a plant stem cell material and wherein the plant stem cell material is stabilized by and encapsulated within a single-layer or bilayer membrane.

2. The elastomeric glove of claim 1, wherein the plant stem cell material is a dedifferentiated plant stem cell material.

3. The elastomeric glove of claim 1, wherein the plant stem cell material is in the form of plant stem cell lysate.

4. The elastomeric glove of claim 1, wherein the plant is selected from: plants of the Rosaceae family, apple varieties, grape varieties, Symphytum, alpine rose, argan trees, dwarf soapwort, tea plants under Family Theaceae, *Aloe Vera* under Family Asphodelaceae, *Citrus* under Family Rutaceae, *Cucumis* under Family Cucurbitaceae, Hibiscus under Family Malvaceae, *Lavandula* under Family Lamiaceae,

*Calendula* under Family Asteraceae, Witch Hazel, Neem trees, Avocado trees and Algae.

5. The elastomeric glove of claim 1, wherein the plant stem cell material is encapsulated by a bilayer membrane system, such that the plant stem cell material is in the form of the bilayer membrane-encapsulated plant stem cell material.

6. The elastomeric glove of claim 5, wherein the bilayer membrane system is selected from the group consisting of liposomes, cerasomes, ethosomes, niosomes, transfersomes, cetosomes, aquasomes, colloidosomes, sphingosomes and cubosomes.

7. The elastomeric glove of claim 5, wherein the bilayer membrane system is liposomes.

8. The elastomeric glove of claim 7, wherein the liposomes have an average diameter in the range of 1-1000 nm.

9. The elastomeric glove of claim 5, wherein the amount of bilayer membrane-encapsulated plant stem cell material is between 0.0001 and 20% by weight of the glove.

10. The elastomeric glove of claim 1, wherein the plant stem cell material is in combination with a phospholipid in the dry coating layer on the surface of the glove.

11. The elastomeric glove of claim 1, comprising two or more plant stem cell materials.

12. The elastomeric glove of claim 1, wherein the amount of plant stem cell material on the surface of the glove is between 0.0001 and 20% by weight of the glove.

13. The elastomeric glove of claim 1, wherein the elastomeric film has an average thickness of between 0.01 and 3.0 mm.

14. The elastomeric glove of claim 1, wherein the elastomer of the elastomeric film is selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

15. The elastomeric glove of claim 1, wherein the dry coating layer is produced from a coating composition with a pH of 5.0 to 8.0.

16. The elastomeric glove of claim 1, wherein the glove has an average thickness of between 0.01 and 3.0 mm, a modulus at 500% of less than 15 MPa, and an elongation at break of at least 500%.

17. A method for the manufacture of the elastomeric glove according to claim 1, the method comprising applying a coating composition containing an effective amount of a plant stem cell material that is stabilized by and encapsulated within a single-layer or bilayer membrane onto a surface of an elastomeric film glove, and drying the coating composition to produce a dry coating layer on the elastomeric film glove.

18. The method of claim 17, wherein the coating composition is applied through a dipping process, spraying method or a tumbling method.

19. The method of claim 18, wherein the coating composition is applied through dipping, and is performed while the elastomeric film glove is on a former, prior to stripping.

20. The method of claim 19, wherein the dipping process to apply the coating composition containing the plant stem cell material onto the surface of the elastomeric film glove is performed after drying and/or curing of the elastomeric film glove, but prior to stripping of the dried and/or cured elastomeric film glove from the former.

21. The method of claim 17, wherein the coating composition containing the plant stem cell material is applied at a temperature of below 40° C.

22. The method of claim 17, wherein the coating composition has a pH of between 5.0 and 8.0.

23. The method of claim 17, wherein the coating composition has a water content of at least 50% by weight at the time of application of the coating composition onto the surface of the elastomeric film glove.

24. The method of claim 23, wherein the coating composition has a water content of at least 90% by weight of the coating composition.

25. The method of claim 23, wherein the coating composition is dried at a temperature below 60° C. to yield the dry coating layer.

26. The method of claim 17, wherein the plant stem cell material is a dedifferentiated plant stem cell material.

27. The method of claim 17, wherein the plant is selected from: plants of the Rosaceae family, apple varieties, grape varieties, Symphytum, alpine rose, argan trees, dwarf soapwort, tea plants under Family Theaceae, *Aloe Vera* under Family Asphodelaceae, *Citrus* under Family Rutaceae, *Cucumis* under Family Cucurbitaceae, Hibiscus under Family Malvaceae, *Lavandula* under Family Lamiaceae, *Calendula* under Family Asteraceae, Witch Hazel, Neem trees, Avocado trees and Algae.

28. The method of claim 17, wherein the plant stem cell material is in the form of plant stem cell lysate.

29. The method of claim 17, wherein the bilayer membrane is selected from the group consisting of liposomes, cerasomes, ethosomes, niosomes, transfersomes, cetosomes, aquasomes, colloidosomes, sphingosomes and cubosomes.

30. The method of claim 17, wherein the bilayer membrane is liposomes, and the encapsulation comprises forming liposomes from the plant stem cell material and a phospholipid.

31. The method of claim 30, wherein the liposomes are formed with an average diameter in the range of 1-1000 nm.

32. The method of claim 17, wherein the coating composition comprises phospholipid.

33. The method of claim 17, wherein the coating composition comprises two or more plant stem cell materials.

34. The method of claim 17, wherein the coating composition is applied in an amount to provide a dry coating layer that constitutes between 0.0001%-20%, by weight of the total weight of the elastomeric glove.

35. The method of claim 17, comprising forming the elastomeric film glove so as to have an average thickness of between 0.01 and 3.0 mm.

36. The method of claim 17, comprising forming the elastomeric film glove from an elastomeric film composition selected from the group consisting of rubber, nitrile rubber, polyurethane, polyisoprene, polychloroprene, acrylic polymers, polybutadienes, copolymers or blends of these polymers, their monomers or other polymers/monomers, and modified forms of these polymers or copolymers.

* * * * *